US007169588B2

(12) United States Patent
Burch et al.

(10) Patent No.: US 7,169,588 B2
(45) Date of Patent: Jan. 30, 2007

(54) BIOCONVERSION OF A FERMENTABLE CARBON SOURCE TO 1,3-PROPANEDIOL BY A SINGLE MICROORGANISM

(75) Inventors: Robert R. Burch, Exton, PA (US); Robert R. Dorsch, Hockessin, DE (US); Lisa Anne Laffend, Claymont, DE (US); Vasantha Nagarajan, Wilmington, DE (US); Charles Nakamura, Claymont, DE (US)

(73) Assignees: E. I. du Pont de Nemours and Company, Wilmington, DE (US); Genencor International, Inc., Palo Alto, CA (US)

( * ) Notice: Subject to any disclaimer, the term of this patent is extended or adjusted under 35 U.S.C. 154(b) by 546 days.

(21) Appl. No.: 10/213,203

(22) Filed: Aug. 5, 2002

(65) Prior Publication Data

US 2003/0082756 A1 May 1, 2003

Related U.S. Application Data

(60) Division of application No. 09/369,796, filed on Aug. 6, 1999, now Pat. No. 6,428,767, which is a continuation-in-part of application No. 08/966,794, filed on Nov. 10, 1997, now Pat. No. 6,025,184, which is a division of application No. 08/440,293, filed on May 12, 1995, now Pat. No. 5,686,276.

(51) Int. Cl.
*C12P 7/18* (2006.01)
*C12N 1/20* (2006.01)
*A61K 51/00* (2006.01)
*C12Q 1/68* (2006.01)

(52) U.S. Cl. .................. 435/158; 435/6; 435/252.31; 435/252.33; 424/1.37

(58) Field of Classification Search .............. 435/6, 435/93, 91.1, 158, 471, 488, 183, 220, 70.1, 435/71.1, 252.31, 252.33, 69.1; 536/23.7, 536/23.2, 23.1; 530/300, 350; 424/1.11, 424/1.37, 1.65, 1.73; 250/281, 282; 935/60
See application file for complete search history.

(56) References Cited

U.S. PATENT DOCUMENTS

| 5,254,467 A | 10/1993 | Kretschmann et al. ...... 435/158 |
| 5,686,276 A | 11/1997 | Laffend et al. ............. 435/158 |
| 5,798,433 A | 8/1998 | Schauhoff et al. |

FOREIGN PATENT DOCUMENTS

| DE | 3734 764 | 10/1987 |
| EP | 0 373 230 | 6/1990 |
| GB | 2 095 267 A | 9/1982 |
| WO | WO-A-91 15590 | 10/1991 |
| WO | WO 96 35796 A | 11/1996 |
| WO | WO 98 21339 | 5/1998 |

OTHER PUBLICATIONS

Tong et al., Applied Biochem. & Biotech., vol. 34/35, pp. 149-159 (1992).*
Daniel Rolf et al., "Growth Temperature-Dependent Activity of Glycerol Dehydratase in *Escherichia coli* Expressing the Citrobacter Freundii dha Regulon", Chemical Abstracts, vol. 118, No. 7, Feb. 15, 1993.
Tong, I Teh et al., "1,3-Propanediol Production by *Escherichia coli* Expressing Genes from the *Klebsiella pneumoniae* dha Regulon", Chemical Abstracts, vol. 116, No. 9, Mar. 2, 1992.
Otto, Karin Elizabeth, "Cloning and Characterization of the Propanediol Dehydratase Genes in *Salmonella typhimurium*", Chemical Abstracts, vol. 120, No. 11, Mar. 14, 1994.
Boenigk, Rainer et al., "Fermentation of Glycerol to 1, 3-Propanediol in Continuous Cultures of Citrobacter Freundii", Chemical Abstracts, vol. 118, No. 17, Apr. 26, 1993.
Veiga da Cunha et al, , *J. Bacteriol* , Sugar-Glycerol Cofermentations in *Lactobacilli*: the Fate of Lactate, 174(3), 1013-1019, 1992.
Tong, I-T et al., *Appl. Biochem. Biotech.*, Enhancement of 1,3-Propanediol Production by Cofermentation in *Escherichia coli* Expressing *Klebsiella pneumoniae* dha Regulon Genes, vol. 34/35, pp. 149-159, 1992.
Tong, I-T., Ph.D.,, Thesis, *University of Wisconsin-Madison*, partial text submitted; full text provided upon request, 1992.
Steib, M. et al. *Arch. Microbiol.*, A new 3-hydroxybutyrate fermenting anaerobe, Ilyobacter polytropus, gen. nov., possing various fermentation pathway, vol. 140, pp. 139-146 (1984).
Talarico, T. L., et al., *Applied and Environmental Microbiology*, Apr. 1990 Utilization of Glycerol as a Hydrogen Acceptor by *Lactobacillus reuteri*: Purification of 1,3-Propanediol: NAD Ocidoreductase, vol. 56, No. 4., p. 943-948.
Sprenger et al., Journal of General Microbiology, Anaerobic Growth of *Escherichia coli* on Glycerol by Importing Genes of the dha Regulon from *Klebsiella pneumoniae*, vol. 135, pp. 1255-1262, 1989.
Daniel, R. et al., J. of Bacteriology, Purification of 1,3-Propanediol Dehydrogenase from *Citrobacter freundii* and Cloning, Sequencing, and Overexpression of Corresponding Gene in *Escherichia coli*, vol. 177(8), 2151-2156(1995).
Tobinatsu, T. et al., *J. Biolog. Chem.*,Molecular Cloning, Sequencing, and Expression of the Genes Encoding Adenosylcobalamin-dependent Diol Dehydrase of *Klebsiella oxytoca*\*270(13), 7142-7148(1995).
Ruch, F. E. et al., *J. Bacteriol.*, Independent Constitutive Expression of the Aerobic and Anaerobic Pathways of Glycerol Catabolism in *Klebsiella aerogenes*, vol. 124(1), 348-352(1975).
Sobolov, M. et al, Metabolism of Glycerol by an Acrolein-Forming *Lactobacillus*, vol. 79, pp. 261-266.
Culp et al., Identification of Isotopically Manipulated Cinnamic Aldehyde and Benzaldehyde, Journal of Agricultural and Food Chemistry, vol. 38, No. 5, 1990, pp. 1249-1255, XP002162148.
Martin et al., Determination of Authenticity of Sake by Carbon Isotope Ratio Anaylsis,Journal of the Association of Official Analytical Chemists. vol. 68, No. 6, 1983, pp. 1405-1408, XP000982801.
Currie et al., Authentication and dating of biomass components of industrial materials; link to sustainable technology, Nuclear Instruments and Methods in Physics Research B—Beam Interactions with Materials and Atoms, vol. 172, Oct. 2000 pp. 281-287, XP000979387.

\* cited by examiner

*Primary Examiner*—Jane Zara

(57) ABSTRACT

A new polypropylene terephthalate composition is provided. The polypropylene terephthalate is comprised of 1,3-propanediol and terephthalate. The 1,3-propanediol is produced by the bioconversion of a fermentatble carbon source, preferable glucose. The resulting polypropylene terephthalate is distinguished from petrochemically produced polymer on the basis of dual carbon-isotopic fingerprinting which indicates both the source and the age of the carbon.

8 Claims, 6 Drawing Sheets

SEQUENCE LISTING

<160> NUMBER OF SEQ ID NOS: 1

<210> SEQ ID NO 1
<211> LENGTH: 12145
<212> TYPE: DNA
<213> ORGANISM: Klebsiella pneumoniae

<400> SEQUENCE: 1

```
gtcgaccacc acggtggtga ctttaatgcc gctctcatgc agcagctcgg tggcggtctc      60
aaaattcagg atgtcgccgg tatagttttt gataatcagc aagacgcctt cgccgccgtc     120
aatttgcatc gcgcattcaa acattttgtc cggcgtcggc gaggtgaata tttcccccgg     180
acaggcgccg gagagcatgc cctggccgat atagccgcag tgcatcggtt catgtccgct     240
gccgccgccg gagagcaggg ccaccttgcc agccaccgga gcgtcggtgc gggtcacata     300
cagcgggtcc tgatgcaggg tcagctgcgg atgggcttta gccagcccct gtaattgttc     360
attcagtaca tcttcaacac ggttaatcag cttttttcatt attcagtgct ccgttggaga     420
aggttcgatg ccgcctctct gctggcggag gcggtcatcg cgtaggggta tcgtctgacg     480
gtggagcgtg cctggcgata tgatgattct ggctgagcgg acgaaaaaaa gaatgccccg     540
acgatcgggt ttcattacga aacattgctt cctgattttg tttctttatg aacgtttttt     600
gctgaggata tggtgaaaat gcgagctggc gcgcttttt tcttctgcca taagcggcgg     660
tcaggatagc cggcgaagcg ggtgggaaaa aattttttgc tgattttctg ccgactgcgg     720
gagaaaaggc ggtcaaacac ggaggattgt aagggcatta tgcggcaaag gagcggatcg     780
ggatcgcaat cctgacagag actagggttt tttgttccaa tatggaacgt aaaaaattaa     840
cctgtgtttc atatcagaac aaaaaggcga agattttttt tgttccctgc ggccctaca      900
gtgatcgcac tgctccggta cgctccgttc aggccgcgct tcactggccg gcgcggataa     960
cgccagggct catcatgtct acatgcgcac ttatttgagg gtgaaaggaa tgctaaaagt    1020
tattcaatct ccagccaaat atcttcaggg tcctgatgct gctgttctgt tcggtcaata    1080
tgccaaaaac ctggcggaga gcttcttcgt catcgctgac gatttcgtaa tgaagctggc    1140
gggagagaaa gtggtgaatg gcctgcagag ccacgatatt cgctgccatg cggaacggtt    1200
taacggcgaa tgcagccatg cggaaatcaa ccgtctgatg gcgattttgc aaaaacaggg    1260
ctgccgcggc gtggtcggga tcggcggtgg taaaaccctc gataccgcga aggcgatcgg    1320
ttactaccag aagctgccgg tggtggtgat cccgaccatc gcctcgaccg atgcgccaac    1380
cagcgcgctg tcggtgatct acaccgaagc gggcgagttt gaagagtatc tgatctatcc    1440
gaaaaacccg gatatggtgg tgatggacac ggcgattatc gccaaagcgc cggtacgcct    1500
gctggtctcc ggcatgggcg atgcgctctc cacctggttc gaggccaaag cttgctacga    1560
tgcgcgcgcc accagcatgg ccggaggaca gtccaccgag gcggcgctga gcctcgcccg    1620
cctgtgctat gatacgctgc tggcggaggg cgaaaaggcc cgtctggcgg cgcaggccgg    1680
ggtagtgacc gaagcgctgg agcgcatcat cgaggcgaac acttacctca gcggcattgg    1740
ctttgaaagc agtggcctgg ccgctgccca tgcaatccac aacggtttca ccattcttga    1800
agagtgccat cacctgtatc acggtgagaa agtggccttc ggtaccctgg cgcagctggt    1860
gctgcagaac agcccgatgg acgagattga acggtgcag gcttctgcc agcgcgtcgg     1920
cctgccggtg acgctcgcgc agatgggcgt caaagagggg atcgacgaga aaatcgccgc    1980
ggtggcgaaa gctacctgcg cggaagggga accatccat aatatgccgt tgcggtgac     2040
cccggagagc gtccatgccg ctatcctcac cgccgatctg ttaggccagc agtggctggc    2100
gcgttaattc gcggtggcta aaccgctggc ccaggtcagc ggttttttctt tctcccctcc    2160
ggcagtcgct gccggagggg ttctctatgg tacaacgcgg aaaggatat gactgttcag     2220
actcaggata ccgggaaggc ggtctcttcc gtcattgccc agtcatggca ccgctgcagc    2280
aagtttatgc agcgcgaaac ctggcaaacg ccgcaccagg cccagggcct gaccttcgac    2340
```

```
tccatctgtc ggcgtaaaac cgcgctgctc accatcggcc aggcggcgct ggaagacgcc    2400
tgggagttta tggacggccg cccctgcgcg ctgtttattc ttgatgagtc cgcctgcatc    2460
ctgagccgtt gcggcgagcc gcaaaccctg gcccagctgg ctgccctggg atttcgcgac    2520
ggcagctatt gtgcggagag cattatcggc acctgcgcg tgtcgctggc cgcgatgcag     2580
ggccagccga tcaacaccgc cggcgatcgg cattttaagc aggcgctaca gccatggagt    2640
ttttgctcga cgccggtgtt tgataaccac gggcggctgt tcggctctat ctcgctttgc    2700
tgtctggtcg agcaccagtc cagcgccgac ctctccctga cgctggccat cgcccgcgag    2760
gtgggtaact ccctgcttac cgacagcctg ctggcggaat ccaaccgtca cctcaatcag    2820
atgtacggcc tgctggagag catggacgat ggggtgatgg cgtggaacga acagggcgtg    2880
ctgcagtttc tcaatgttca ggcggcgaga ctgctgcatc ttgatgctca ggccagccag    2940
gggaaaaata tcgccgatct ggtgaccctc ccggcgctgc tgcgccgcgc catcaaacac    3000
gcccgcggcc tgaatcacgt cgaagtcacc tttgaaagtc agcatcagtt tgtcgatgcg    3060
gtgatcacct taaaaccgat tgtcgaggcg caaggcaaca gttttattct gctgctgcat    3120
ccggtggagc agatgcggca gctgatgacc agccagctcg gtaaagtcag ccacaccttt    3180
gagcagatgt ctgccgacga tccggaaacc cgacgcctga tccactttgg ccgccaggcg    3240
gcgcgcggcg gcttcccggt gctactgtgc ggcgaagagg gggtcgggaa agagctgctg    3300
agccaggcta ttcacaatga aagcgaacgg gcgggcggcc cctacatctc cgtcaactgc    3360
cagctatatg ccgacagcgt gctgggccag gactttatgg gcagcgcccc taccgacgat    3420
gaaaatggtc gcctgagccg ccttgagctg gccaacggcg gcaccctgtt tctggaaaag    3480
atcgagtatc tggcgccgga gctgcagtcg gctctgctgc aggtgattaa gcagggcgtg    3540
ctcacccgcc tcgacgcccg gcgcctgatc ccggtggatg tgaaggtgat tgccaccacc    3600
accgtcgatc tggccaatct ggtggaacag aaccgcttta gccgccagct gtactatgcg    3660
ctgcactcct ttgagatcgt catcccgccg ctgcgcgccc gacgcaacag tattccgtcg    3720
ctggtgcata accggttgaa gagcctggag aagcgtttct cttcgcgact gaaagtggac    3780
gatgacgcgc tggcacagct ggtggcctac tcgtggccgg ggaatgattt tgagctcaac    3840
agcgtcattg agaatatcgc catcagcagc gacaacggcc acattcgcct gagtaatctg    3900
ccggaatatc tcttttccga gcggccgggc ggggatagcg cgtcatcgct gctgccggcc    3960
agcctgactt ttagcgccat cgaaaaggaa gctattattc acgccgcccg ggtgaccagc    4020
gggcgggtgc aggagatgtc gcagctgctc aatatcggcc gcaccaccct gtggcgcaaa    4080
atgaagcagt acgatattga cgccagccag ttcaagcgca agcatcaggc ctagtctctt    4140
cgattcgcgc catggagaac agggcatccg acaggcgatt gctgtagcgt ttgagcgcgt    4200
cgcgcagcgg atgcgcgcgg tccatggccg tcagcaggcg ttcgagccga cgggactggg    4260
tgcgcgccac gtgcagctgg gcagaggcga gattcctccc cgggatcacg aactgttta    4320 acgggccgct ctcggccata ttgcggtcga taagccgctc cagggcggtg atctcctctt    4380
cgccgatcgt ctggctcagg cgggtcaggc cccgcgcatc gctggccagt tcagccccca    4440
gcacgaacag cgtctgctga atatggtgca ggctttcccg cagcccggcg tcgcgggtcg    4500
tggcgtagca cacgcccagc tgggatatca gttcatcgac ggtgccgtag gcctcgacgc    4560
gaatatggtc tttctcgatg cggctgccgc cgtacagggc ggtggtgcct ttatccccgg    4620
tgcgggtata gatacgatac attcagtttc tctcacttaa cggcaggact ttaaccagct    4680
gcccggcgtt ggcgccgagc gtacgcagtt gatcgtcgct atcggtgacg tgtccggtag    4740
```

-continued

```
ccagcggcgc gtccgccggc agctgggcat gagtgagggc tatctcgccg gacgcgctga   4800
gcccgatacc cacccgcagg ggcgagcttc tggccgccag ggcgcccagc gcagcggcgt   4860
caccgcctcc gtcataggtt atggtctggc aggggacccc ctgctcctcc agccccagc    4920 acagctcatt gatggcgccg gcatggtgcc cgcgcggatc gtaaaacagg cgtacgcctg   4980
gcggtgaaag cgacatgacg gtcccctcgt taacactcag aatgcctggc ggaaaatcgc   5040
ggcaatctcc tgctcgttgc ctttacgcgg gttcgagaac gcattgccgt cttttagagc   5100
catctccgcc atgtagggga agtcggcctc ttttacccce agatcgcgca gatgctgcgg   5160
aataccgata tccatcgaca gacgcgtgat agcggcgatg gcttttccg  ccgcgtcgag   5220 agtggacagt ccggtgatat tttcgcccat cagttcagcg atatcggcga atttctccgg   5280
gttggcgatc aggttgtagc gcgccacatg cggcagcagg acagcgttgg ccacgccgtg   5340
cggcatgtcg tacaggccgc ccagctggtg cgccatggcg tgcacgtagc cgaggttggc   5400
gttattgaaa gccatcccgg ccagcagaga agcataggcc atgttttccc gcgcctgcag   5460
attgctgccg agggccacgg cctggcgcag gttgcgggcg atgaggcgga tcgcctgcat   5520
ggcggcggcg tccgtcaccg ggttagcgtc tttggagata taggcctcta cggcgtgggt   5580
cagggcatcc atcccggtcg ccgcggtcag ggcggccggt ttaccgatca tcagcagtgg   5640
atcgttgata gagaccgacg gcagtttgcg ccagctgacg atcacaaact tcactttggt   5700
ttcggtgttg gtcaggacgc agtggcgggt gacctcgctg gcggtgccgg cggtggtatt   5760
gaccgcgacg ataggcggca gcgggttggt cagggtctcg attccggcat actggtacag   5820
atcgccctca tgggtggcgg cgatgccgat gcctttgccg caatcgtgcg ggctgccgcc   5880
gcccacggtg acgatgatgt cgcactgttc gcggcgaaac acggcgaggc cgtcgcgcac   5940
gttggtgtct ttcgggttcg gctcgacgcc gtcaaagatc gccacctcga tcccggcctc   6000
ccgcagataa tgcagggttt tgtccaccgc gccatcttta attgcccgca ggcctttgtc   6060
ggtgaccagc agggctttttt tccccccag  cagctggcag cgttcgccga ctacggaaat   6120
ggcgttgggg ccaaaaaagt taacgtttgg caccagataa tcaaacatac gatagctcat   6180
aatataccct ctcgcttcag gttataatgc ggaaaaacaa tccagggcgc actgggctaa   6240
taattgatcc tgctcgaccg taccgccgct aacgccgacg cgccaattca cctgctcatt   6300
aaaaataact ggcaggccgc cgccaaaaat aataattcgc tgttggttgg ttagctgcag   6360
accgtacaga gattgtcctg gctgaccgc  tgacgtaatt tcatgggtac cttgcttcag   6420
gctgcaggcg ctccaggctt tattcaggga atatcgcag  ctggagacga aggcctcgtc   6480
catccgctgg ataagcagcg tgttgcctcc gcggtcaact acggaaaaca ccaccgccac   6540
gttgatctca gtggcttttt tttccaccgc cgccgccatt tgctgggcgg cggccagggt   6600
gattgtctga acttgttggc tcttgttcat cattctctcc cgcaccagga taacgctggc   6660
gcgaatagtc gtaggggggc gatagtaaaa actattacc  attcggttgg cttgcttttat   6720 ttttgtcagc gttatttttgt cgcccgccat gatttagtca ataggggttaa aatagcgtcg   6780 gaaaacgta  attaagggcg ttttttatta attgatttat atcattgcgg gcgatcacat   6840
tttttatttt tgccgccgga gtaaagtttc atagtgaaac tgtcggtaga tttcgtgtgc   6900
caaattgaaa cgaaattaaa tttattttttt tcaccactgg ctcatttaaa gttccgctat   6960
tgccggtaat ggccgggcgg caacgacgct ggcccggcgt attcgctacc gtctgcggat   7020
ttcacctttt gagccgatga acaatgaaaa gatcaaaacg atttgcagta ctggcccagc   7080
gccccgtcaa tcaggacggg ctgattggcg agtggcctga agagggggctg atcgccatgg   7140
```

-continued

| | |
|---|---|
| acagcccctt tgacccggtc tcttcagtaa aagtggacaa cggtctgatc gtcgaactgg | 7200 |
| acggcaaacg ccgggaccag tttgacatga tcgaccgatt tatcgccgat tacgcgatca | 7260 |
| acgttgagcg cacagagcag gcaatgcgcc tggaggcggt ggaaatagcc cgtatgctgg | 7320 |
| tggatattca cgtcagccgg gaggagatca ttgccatcac taccgccatc acgccggcca | 7380 |
| aagcggtcga ggtgatggcg cagatgaacg tggtggagat gatgatgcg ctgcagaaga | 7440 |
| tgcgtgcccg ccggacccccc tccaaccagt gccacgtcac caatctcaaa gataatccgg | 7500 |
| tgcagattgc cgctgacgcc gccgaggccg ggatccgcgg cttctcagaa caggagacca | 7560 |
| cggtcggtat cgcgcgctac gcgccgttta acgccctggc gctgttggtc ggttcgcagt | 7620 |
| gcggccgccc cggcgtgttg acgcagtgct cggtggaaga ggccaccgag ctggagctgg | 7680 |
| gcatgcgtgg cttaaccagc tacgccgaga cggtgtcggt ctacggcacc gaagcggtat | 7740 |
| ttaccgacgg cgatgatacg ccgtggtcaa aggcgttcct cgcctcggcc tacgcctccc | 7800 |
| gcgggttgaa aatgcgctac acctccggca ccggatccga agcgctgatg ggctattcgg | 7860 |
| agagcaagtc gatgctctac ctcgaatcgc gctgcatctt cattactaaa ggcgccgggg | 7920 |
| ttcagggact gcaaaacggc gcggtgagct gtatcggcat gaccggcgct gtgccgtcgg | 7980 |
| gcattcgggc ggtgctggcg gaaaacctga tcgcctctat gctcgacctc gaagtggcgt | 8040 |
| ccgccaacga ccagactttc tcccactcgg atattgccg caccgcgcgc accctgatgc | 8100 |
| agatgctgcc gggcaccgac tttattttct ccggctacag cgcggtgccg aactacgaca | 8160 |
| acatgttcgc cggctcgaac ttcgatgcgg aagattttga tgattacaac atcctgcagc | 8220 |
| gtgacctgat ggttgacggc ggcctgcgtc cggtgaccga ggcggaaacc attgccattc | 8280 |
| gccagaaagc ggcgcgggcg atccaggcgg ttttccgcga gctggggctg ccgccaatcg | 8340 |
| ccgacgagga ggtggaggcc gccacctacg cgcacggcag caacgagatg ccgccgcgta | 8400 |
| acgtggtgga ggatctgagt gcggtggaag agatgatgaa gcgcaacatc accggcctcg | 8460 |
| atattgtcgg cgcgctgagc cgcagcggct ttgaggatat cgccagcaat attctcaata | 8520 |
| tgctgcgcca gcgggtcacc ggcgattacc tgcagacctc ggccattctc gatcggcagt | 8580 |
| tcgaggtggt gagtgcggtc aacgacatca atgactatca ggggccgggc accggctatc | 8640 |
| gcatctctgc cgaacgctgg gcggagatca aaaatattcc gggcgtggtt cagcccgaca | 8700 |
| ccattgaata aggcggtatt cctgtgcaac agacaaccca aattcagccc tcttttaccc | 8760 |
| tgaaacccg cgagggcggg gtagcttctg ccgatgaacg cgccgatgaa gtggtgatcg | 8820 |
| gcgtcggccc tgccttcgat aaacaccagc atcacactct gatcgatatg ccccatggcg | 8880 |
| cgatcctcaa agagctgatt gccgggggtgg aagaagaggg gcttcacgcc cgggtggtgc | 8940 |
| gcattctgcg cacgtccgac gtctccttta tggcctggga tgcggccaac ctgagcggct | 9000 |
| cggggatcgg catcggtatc cagtcgaagg ggaccacggt catccatcag cgcgatctgc | 9060 |
| tgccgctcag caacctggag ctgttctccc aggcgccgct gctgacgctg agacctacc | 9120 |
| ggcagattgg caaaaacgct gcgcgctatg cgcgcaaaga gtcaccttcg ccggtgccgg | 9180 |
| tggtgaacga tcagatggtg cggccgaaat ttatggccaa agccgcgcta tttcatatca | 9240 |
| aagagaccaa acatgtggtg caggacgccg agcccgtcac cctgcacatc gacttagtaa | 9300 |
| gggagtgacc atgagcgaga aaaccatgcg cgtgcaggat tatccgttag ccacccgctg | 9360 |
| cccggagcat atcctgacgc ctaccggcaa accattgacc gatattaccc tcgagaaggt | 9420 |
| gctctctggc gaggtgggcc cgcaggatgt gcggatctcc cgccagaccc ttgagtacca | 9480 |
| ggcgcagatt gccgagcaga tgcagcgcca tgcggtggcg cgcaatttcc gccgcgcggc | 9540 |

-continued

```
ggagcttatc gccattcctg acgagcgcat tctggctatc tataacgcgc tgcgcccgtt    9600
ccgctcctcg caggcggagc tgctggcgat cgccgacgag ctggagcaca cctggcatgc    9660
gacagtgaat gccgcctttg tccgggagtc ggcggaagtg tatcagcagc ggcataagct    9720
gcgtaaagga agctaagcgg aggtcagcat gccgttaata ccgggattg atatcggcaa     9780 cgccaccacc gaggtggcgc tggcgtccga ctacccgcag gcgagggcgt ttgttgccag    9840
cgggatcgtc gcgacgacgg gcatgaaagg acgcgggac aatatcgccg ggaccctcgc     9900
cgcgctggag caggccctgg cgaaaacacc gtggtcgatg agcgatgtct ctcgcatcta    9960
tcttaacgaa gccgcgccgg tgattggcga tgtggcgatg agaccatca ccgagaccat    10020 tatcaccgaa tcgaccatga tcggtcataa cccgcagacg ccgggcgggg tgggcgttgg   10080
cgtggggacg actatcgccc tcgggcggct ggcgacgctg ccggcggcgc agtatgccga   10140
ggggtggatc gtactgattg acgacgccgt cgatttcctt gacgccgtgt ggtggctcaa   10200
tgaggcgctc gaccggggga tcaacgtggt ggcggcgatc ctcaaaaagg acgacggcgt   10260
gctggtgaac aaccgcctgc gtaaaaccct gccggtggtg gatgaagtga cgctgctgga   10320
gcaggtcccc gaggggtaa tggcggcggt ggaagtggcc gcgccgggcc aggtggtgcg    10380
gatcctgtcg aatccctacg ggatcgccac cttcttcggg ctaagcccgg aagagaccca   10440
ggccatcgtc cccatcgccc gcgccctgat tggcaaccgt tccgcggtgg tgctcaagac   10500
cccgcagggg gatgtgcagt cgcgggtgat cccggcgggc aacctctaca ttagcggcga   10560
aaagcgccgc ggagaggccg atgtcgccga gggcgcggaa gccatcatgc aggcgatgag   10620
cgcctgcgct ccggtacgcg acatccgcgg cgaaccgggc acccacgccg gcggcatgct   10680
tgagcgggtc gcaaggtaa tggcgtccct gaccggccat gagatgagcg cgatatacat    10740
ccaggatctg ctggcggtgg atacgtttat tccgcgcaag gtgcagggcg ggatggccgg   10800
cgagtgcgcc atggagaatg ccgtcgggat ggcggcgatg gtgaaagcgg atcgtctgca   10860
aatgcaggtt atcgcccgcg aactgagcgc ccgactgcag accgaggtgg tggtgggcgg   10920
cgtggaggcc aacatggcca tcgccggggc gttaaccact cccggctgtg cggcgccgct   10980
ggcgatcctc gacctcggcg ccggctcgac ggatgcggcg atcgtcaacg cggaggggca   11040
gataacggcg gtccatctcg ccggggcggg gaatatggtc agcctgttga ttaaaaccga   11100
gctgggcctc gaggatcttt cgctggcgga agcgataaaa aaatacccgc tggccaaagt   11160
ggaaagcctg ttcagtattc gtcacgagaa tggcgcggtg gagttctttc gggaagccct   11220
cagcccggcg gtgttcgcca agtggtgta catcaaggag ggcgaactgg tgccgatcga    11280
taacgccagc ccgctggaaa aaattcgtct cgtgcgccgg caggcgaaag agaaagtgtt   11340
tgtcaccaac tgcctgcgcg cgctgcgcca ggtctcaccc ggcggttcca ttcgcgatat   11400
cgcctttgtg gtgctggtgg gcggctcatc gctggacttt gagatcccgc agcttatcac   11460
ggaagccttg tcgcactatg gcgtggtcgc cgggcagggc aatattcggg aacagaagg    11520 gccgcgcaat gcggtcgcca ccgggctgct actggccggt caggcgaatt aaacgggcgc   11580
tcgcgccagc ctctctcttt aacgtgctat ttcaggatgc cgataatgaa ccagacttct   11640
accttaaccg ggcagtgcgt ggccgagttt cttggcaccg gattgctcat tttcttcggc   11700
gcgggctgcg tcgctgcgct gcgggtcgcc ggggccagct ttggtcagtg ggagatcagt   11760
attatctggg gccttggcgt cgccatggcc atctacctga cggccggtgt ctccggcgcg   11820
cacctaaatc cggcggtgac cattgccctg tggctgttcg cctgttttga acgccgcaag   11880
gtgctgccgt ttattgttgc ccagacggcc gggcctttct gcgccgccgc gctggtgtat   11940
```

```
                                                        -continued gggctctatc gccagctgtt tctcgatctt gaacagagtc agcatatcgt gcgcggcact  12000
gccgccagtc ttaacctggc cggggtcttt tccacgtacc cgcatccaca tatcactttt  12060
atacaagcgt ttgccgtgga gaccaccatc acggcaatcc tgatggcgat gatcatggcc  12120
ctgaccgacg acggcaacgg aattc                                        12145
```

US 7,169,588 B2

BIOCONVERSION OF A FERMENTABLE CARBON SOURCE TO 1,3-PROPANEDIOL BY A SINGLE MICROORGANISM

This is a divisional application of U.S. Application No. 09/369,796, filed 6 Aug. 1999, now issued as U.S. Pat. No. 6,428,767 on 6 Aug. 2002, which in turn is a CIP of U.S. Application No. 08/966,794, filed 10 Nov. 1997, which is a divisional application of U.S. Patent Application No. 08/440,293, filed 12 May 1995, now U.S. Pat. No. 5,686,276.

FIELD OF INVENTION

The invention relates to a new 1,3-propanediol monomer and polymers derived from these monomers. More specifically, polypropylene terephthalate has been produced from a 1,3-propanediol monomer prepared by bioconverting a fermentable carbon source directly to 1,3-propanediol using a single microorganism.

BACKGROUND 1,3-Propanediol is a monomer useful in the production of polyester fibers and in the manufacture of polyurethanes.

It has been known for over a century that 1,3-propanediol can be produced from the fermentation of glycerol. Bacterial strains able to produce 1,3-propanediol have been found, for example, in the groups *Citrobacter, Clostridium, Enterobacter, Ilyobacter, Klebsiella, Lactobacillus,* and *Pelobacter*. In each case studied, glycerol is converted to 1,3-propanediol in a two step, enzyme-catalyzed reaction sequence. In the first step, a dehydratase catalyzes the conversion of glycerol to 3-hydroxypropionaldehyde (3-HP) and water, Equation 1. In the second step, 3-HP is reduced to 1,3-propanediol by a NAD$^+$-linked oxidoreductase, Equation 2. The 1,3-propanediol is not metabolized further and, as a result,

Glycerol→3-HP+H$_2$O             (Equation 1)

3-HP+NADH+H$^+$→1,3-Propanediol+NAD$^+$             (Equation 2)

accumulates in high concentration in the media. The overall reaction consumes a reducing equivalent in the form of a cofactor, reduced β-nicotinamide adenine dinucleotide (NADH), which is oxidized to nicotinamide adenine dinucleotide (NAD$^+$).

The production of 1,3-propanediol from glycerol is generally performed under anaerobic conditions using glycerol as the sole carbon source and in the absence of other exogenous reducing equivalent acceptors. Under these conditions in e.g., strains of *Citrobacter, Clostridium,* and *Klebsiella*, a parallel pathway for glycerol operates which first involves oxidation of glycerol to dihydroxyacetone (DHA) by a NAD$^+$-(or NADP$^+$-) linked glycerol dehydrogenase, Equation 3. The DHA, following phosphorylation to dihydroxyacetone phosphate (DHAP) by a DHA kinase (Equation 4),

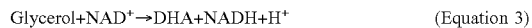

Glycerol+NAD$^+$→DHA+NADH+H$^+$             (Equation 3)

DHA+ATP→DHAP+ADP             (Equation 4)

becomes available for biosynthesis and for supporting ATP generation via e.g., glycolysis. In contrast to the 1,3-propanediol pathway, this pathway may provide carbon and energy to the cell and produces rather than consumes NADH.

In *Klebsiella pneumoniae* and *Citrobacter freundii,* the genes encoding the functionally linked activities of glycerol dehydratase (dhaB), 1,3-propanediol oxidoreductase (dhaT), glycerol dehydrogenase (dhaD), and dihydroxyacetone kinase (dhaK) are encompassed by the dha regulon. The dha regulons from *Citrobacter* and *Klebsiella* have been expressed in *Escherichia coli* and have been shown to convert glycerol to 1,3-propanediol.

Although biological methods of both glycerol and 1,3-propanediol production are known, it has never been demonstrated that the entire process can be accomplished by a single organism.

Neither the chemical nor biological methods described above for the production of 1,3-propanediol is well suited for industrial scale production. This is because the chemical processes are energy intensive and the biological processes require glycerol, an expensive starting material. A method requiring low energy input and an inexpensive starting material is needed. A more desirable process would incorporate a microorganism that would have the ability to convert basic carbon sources, such as carbohydrates or sugars, to the desired 1,3-propanediol end-product.

There are several difficulties that are encountered when attempting to biologically producte 1,3-propanediol by a single organism from an inexpensive carbon substrate such as glucose or other sugars. The biological production of 1,3-propanediol requires glycerol as a substrate for a two-step sequential reaction in which a dehydratase enzyme (typically a coenzyme B$_{12}$-dependent dehydratase) converts glycerol to an intermediate, 3-hydroxypropionaldehyde, which is then reduced to 1,3-propanediol by a NADH- (or NADPH) dependent oxidoreductase. The complexity of the cofactor requirements necessitates the use of a whole cell catalyst for an industrial process which utilizes this reaction sequence for the production of 1,3-propanediol. Furthermore, in order to make the process economically viable, a less expensive feedstock than glycerol or dihydroxyacetone is needed. Glucose and other carbohydrates are suitable substrates, but, as discussed above, are known to interfere with 1,3-propanediol production.

SUMMARY OF THE INVENTION

The present invention provides a 1,3-propanediol composition of matter produced by the process comprising the bioconversion of a carbon substrate, other than glycerol or dehydroxy acetone dihydroxyacetone, to 1,3-propanediol by a single microorganism having at least one gene that expresses a dehydratase enzyme by contacting said microorganism with said substrate.

The invention further provides a biosourced 1,3-propanediol composition of matter having δ$^{13}$C of about −10.9 to about −15.4, preferably about −13.22 to about −14.54, and most preferably about −13.84 to about −13.92, and a f$_M$ $^{14}$C of about 1.04 to about 1.18, preferably about 1.106 to about 1.129, and most preferably about 1.111 to about 1.124.

Additionally the invention provides a polymer comprising at least two repeating units of biosourced 1,3-propanediol, characterized by a δ$^{13}$C of −10.74 to about −17.02, preferably about −13.22 to about −14.54, and most preferably about −13.84 to about −13.82 to about −13.94, and a f$_M$ $^{14}$C of about 1.003 to about 1.232, preferably about 1.106 to about 1.129, and most preferably about 1.111 to about 1.124.

In another embodiment, the invention provides a polymer comprising at least two repeating units of biosourced polypropylene terephthalate, characterized by a δ$^{13}$C of about −24.74 to about −24.88, and a f$_M$ $^{14}$C of about 0.299 to about 0.309 and a polymeric unit consisting of polypropylene terephthalate having a $\delta^{13}C$ of about −24.74 to about −24.88, and a $f_M$ $^{14}C$ of about 0.299 to about 0.309.

In another embodiment the invention provides a method for identifying the presence of a biosourced 1,3-propanediol in a sample, the method comprising (a) purifying the 1,3-propanediol from the sample; and (b) determining the $\delta^{13}C$ and $f_M$ $^{14}C$ characterizing the sample of step (a), wherein a $\delta^{13}C$ of about −10.9 to about −15.4 and a $f_M$ $^{14}C$ of about 1.04 to about 1.18 indicates the presence of a biosourced 1,3-propanediol. Additionally, the specific source of biosourced carbon (e.g. glucose or gycerol) can be ascertained by dual carbon-isotopic analysis.

Finally, the invention provides an article of manufacture comprising the described composition produced by the process and in a form selected from the group consisting of a film, a fiber, a particle, and a molded article.

BRIEF DESCRIPTION OF BIOLOGICAL DEPOSITS

Figure 1:
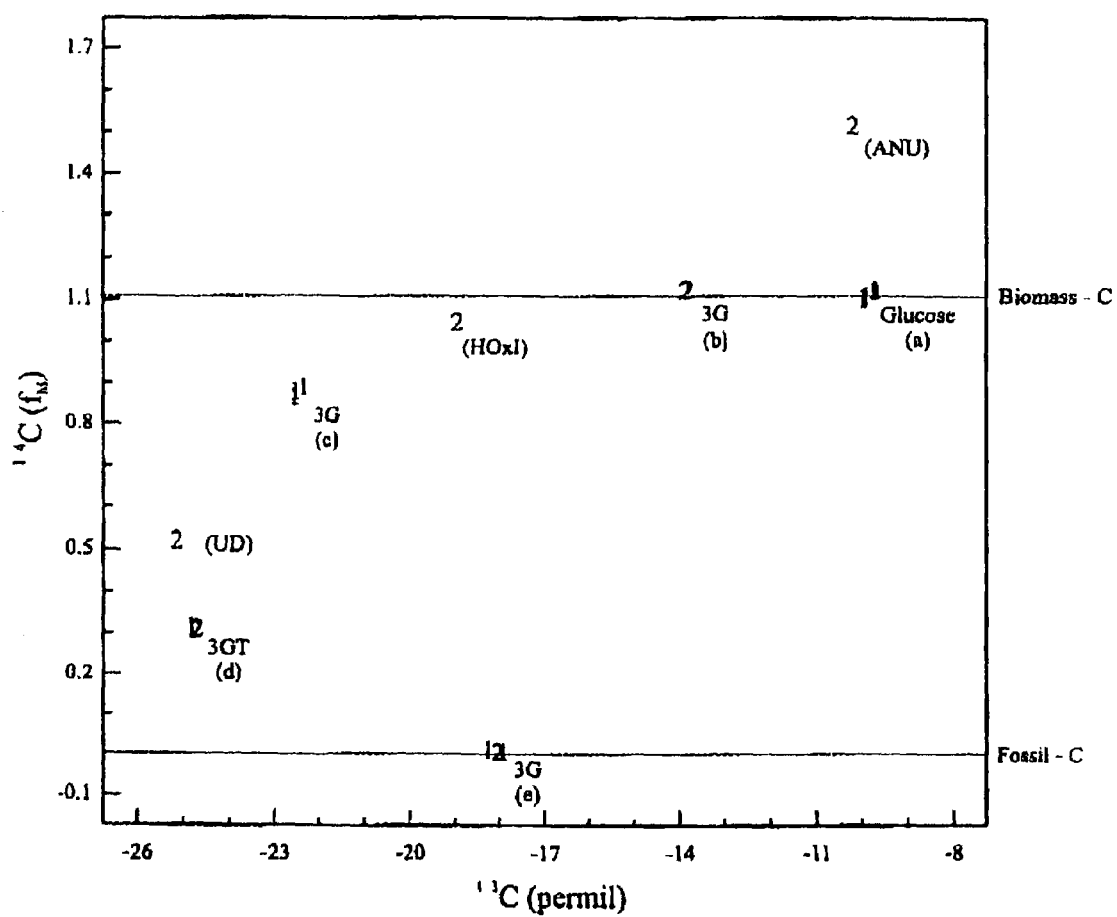
FIG. 1 shows the dual isotope diagram of the data in Table 1. The abscissa gives the values of $\delta^{13}C$ (per mil) referenced to PDB. The ordinate gives $^{14}C$ expressed as $f_M$ (fraction of modern).
Figure 2:
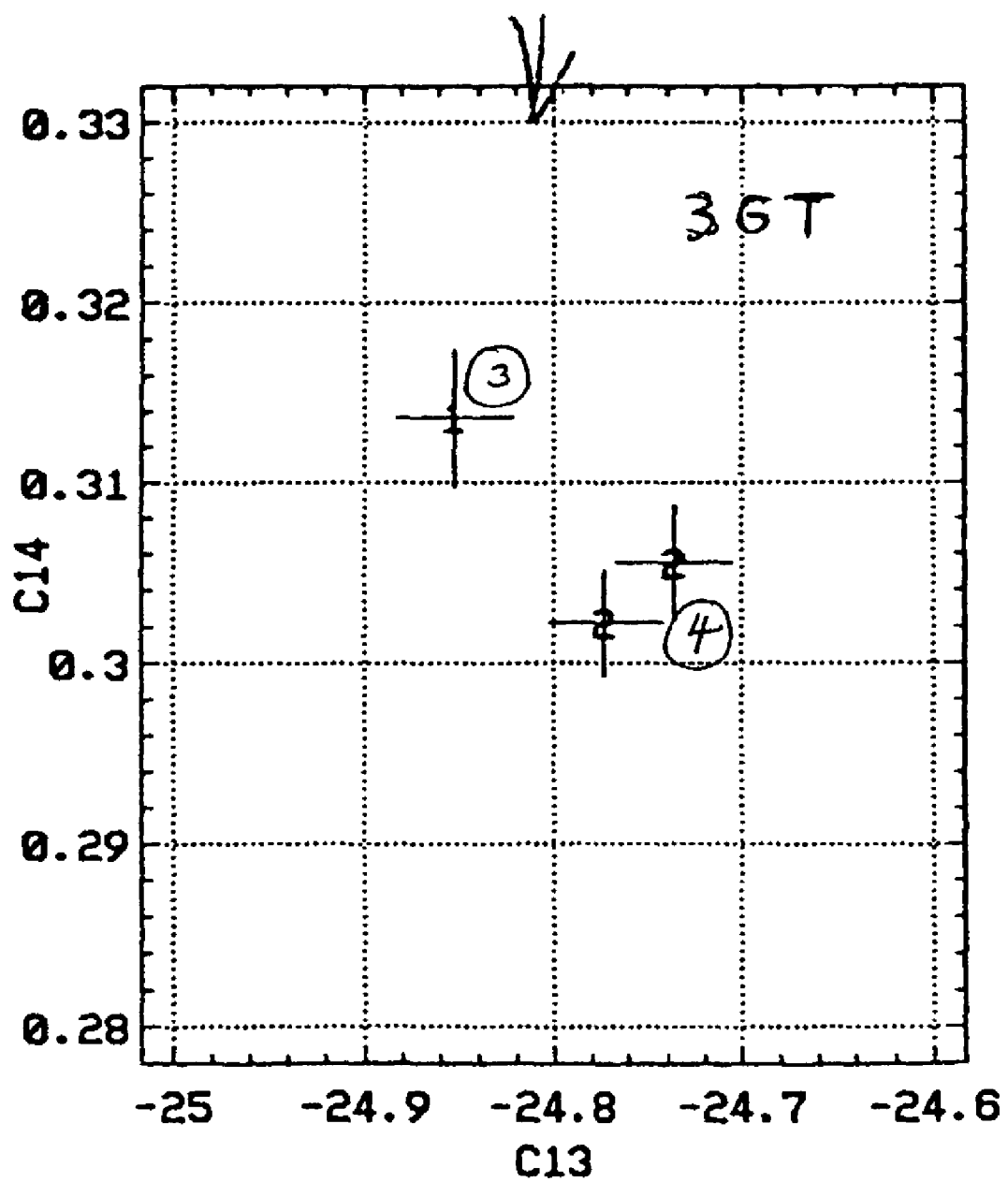
FIG. 2, an expanded view of FIG. 1, shows the individual values for the two polypropylene terephthalate samples prepared with biosourced 1,3-propanediol. Error bars reflect the standard uncertainties for each isotope.
Figure 3:
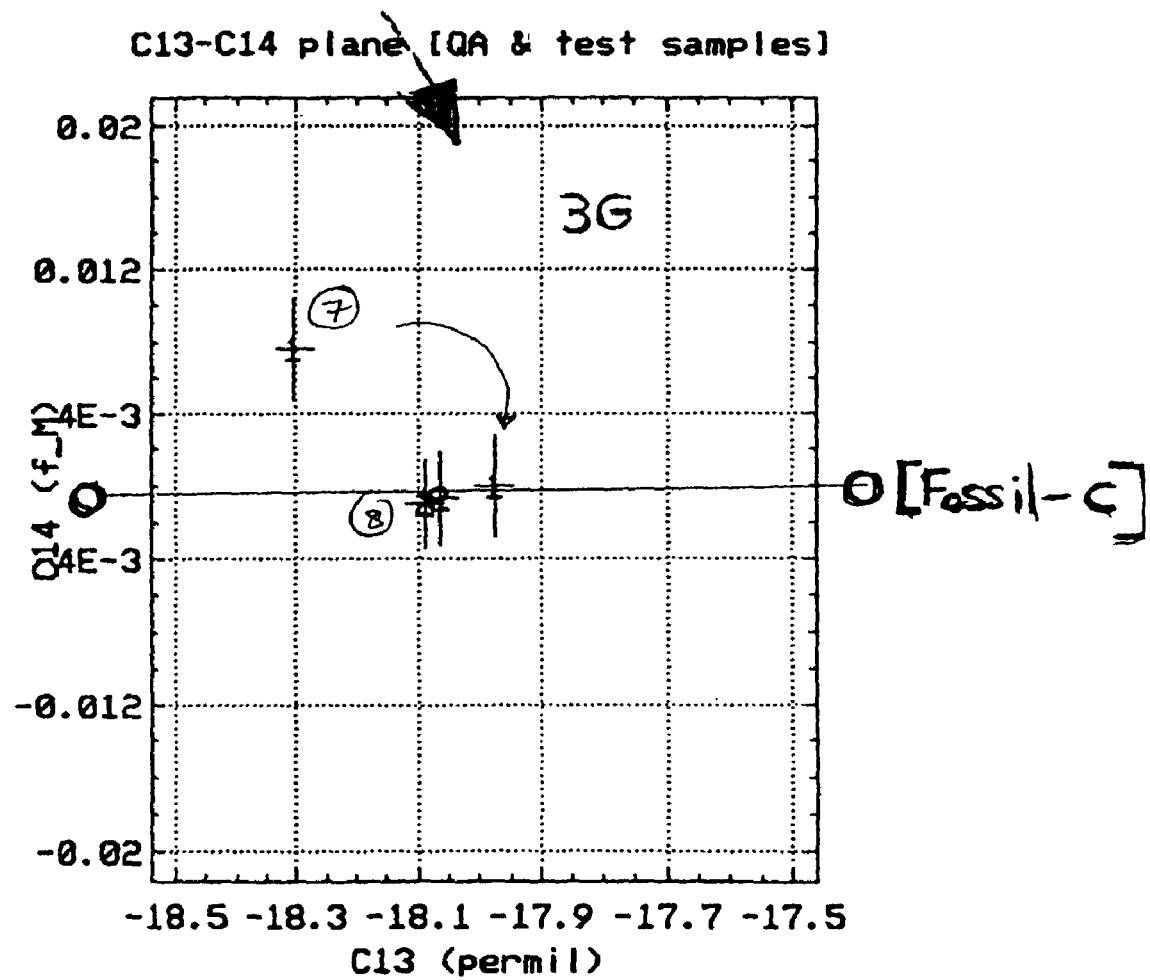
FIG. 3, an expanded view of FIG. 1, shows the individual values for the two biosourced 1,3-propanediol samples. Error bars reflect the standard uncertainties for each isotope.
Figure 4:
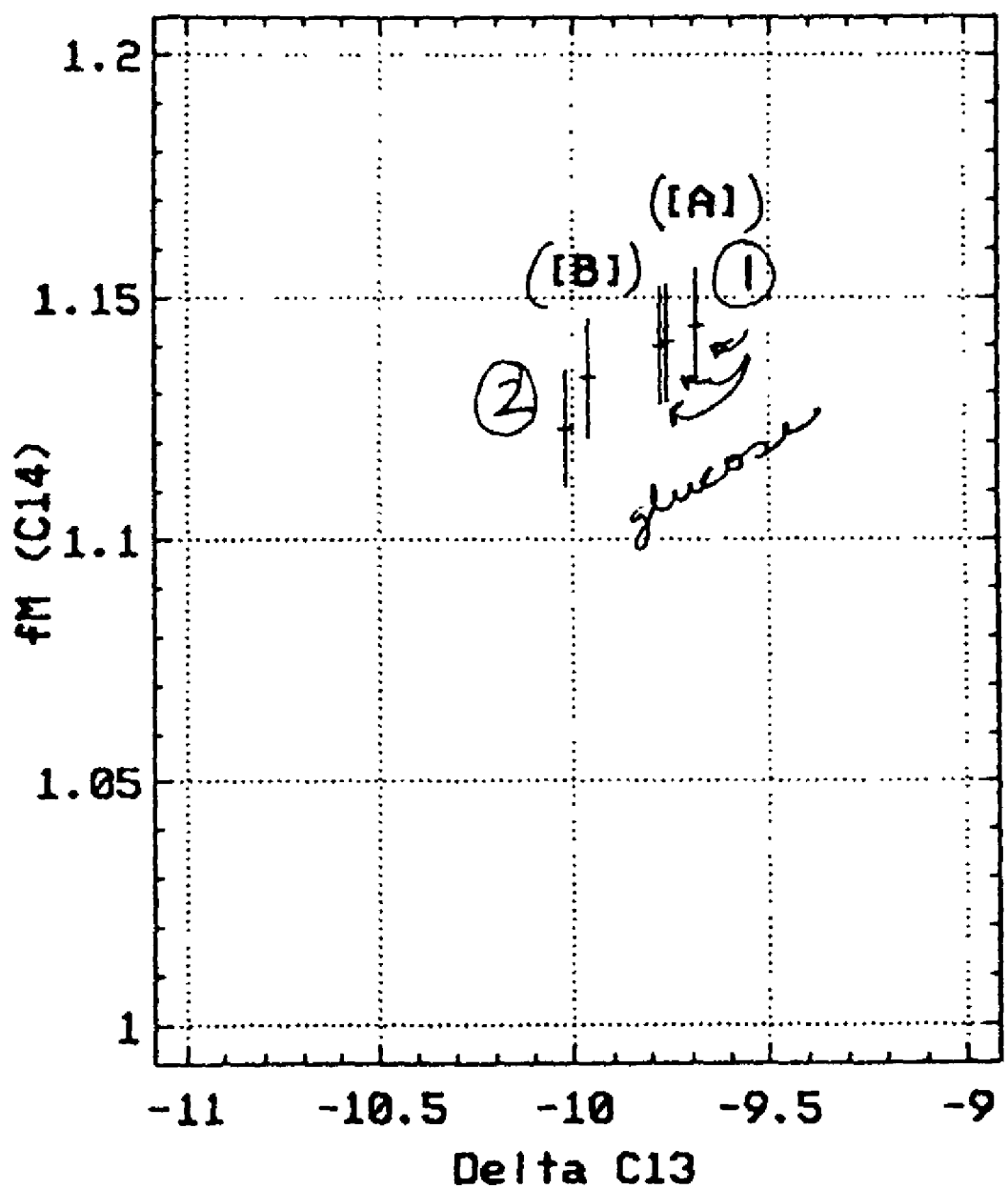
FIG. 4, an expanded view of FIG. 1, shows the individual values for the two glucose samples. Error bars reflect the standard uncertainties for each isotope.
Figure 5:
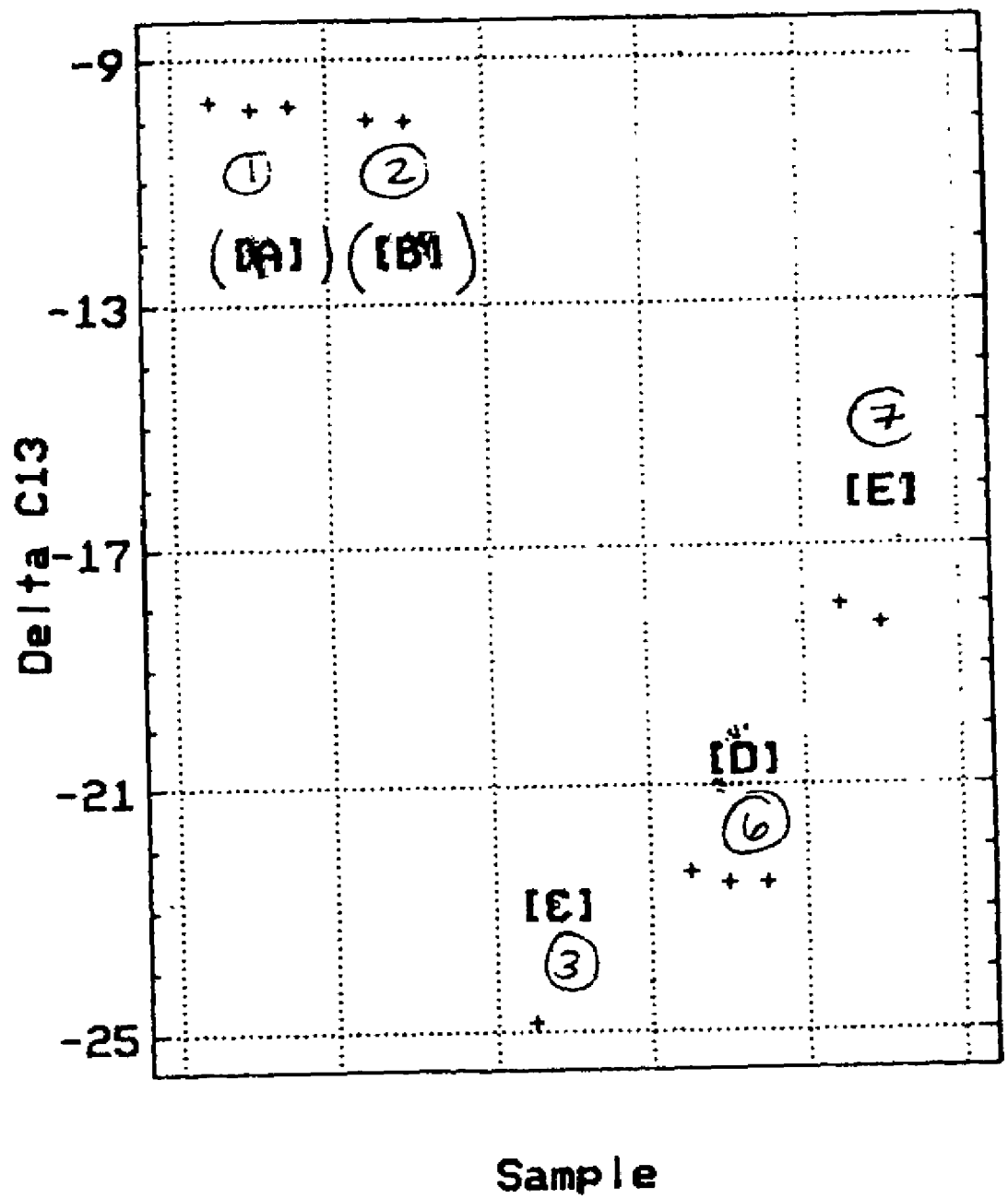
FIG. 5 shows $^{14}C$ precision data for selected samples.
Figure 6:
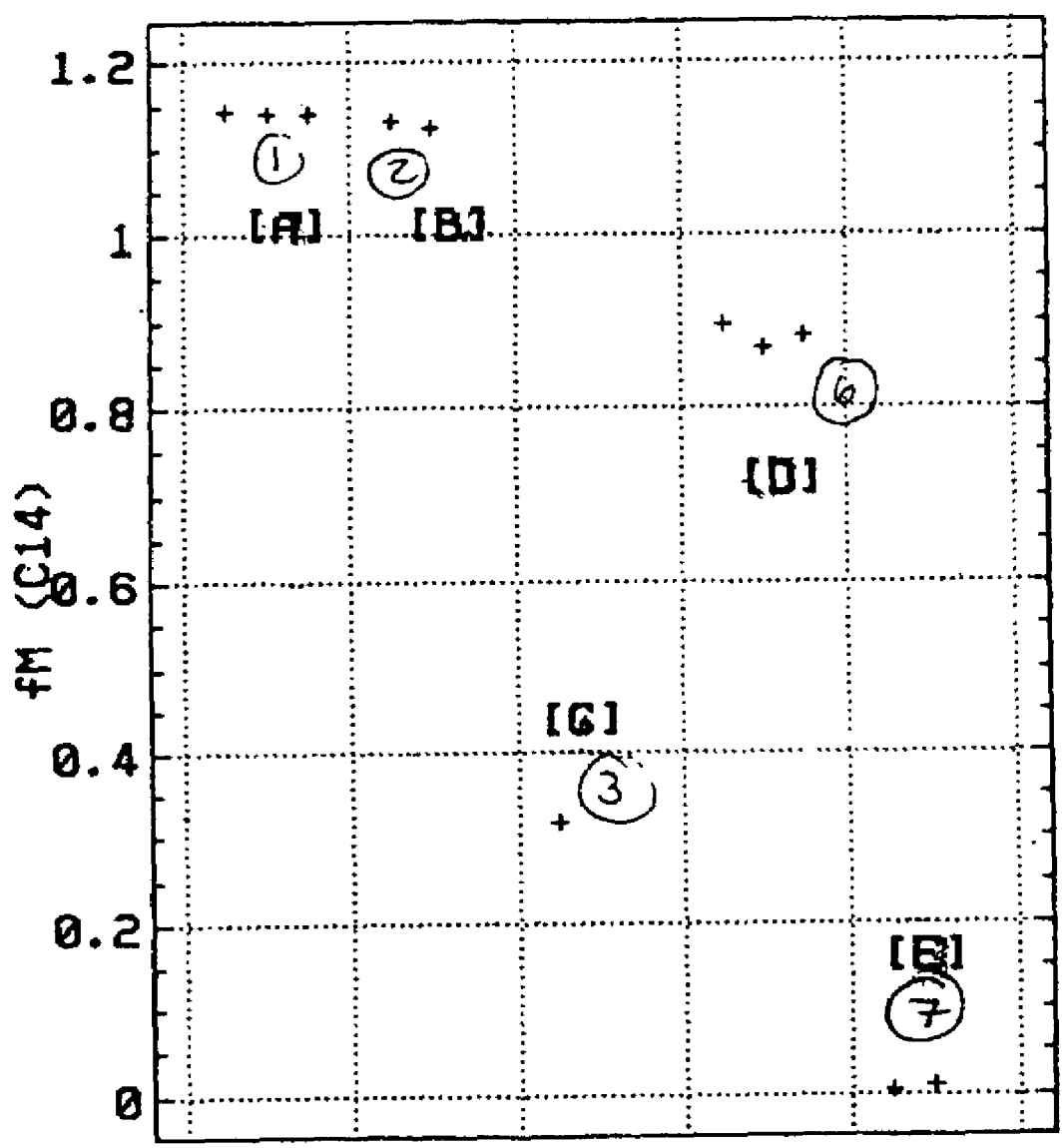
FIG. 6 shows $^{13}C$ precision data for selected samples.

The transformed *E. coli* DH5α containing cosmid pKP1 containing a portion of the *Klebsiella* genome encoding the glycerol dehydratase enzyme was deposited on Apr. 18, 1995 with the ATCC under the terms of the Budapest Treaty and is identified by the ATCC number ATCC 69789. The transformed *E. coli* DH5α containing cosmid pKP4 containing a portion of the *Klebsiella* genome encoding a diol dehydratase enzyme was deposited on Apr. 18, 1995 with the ATCC under the terms of the Budapest Treaty and is identified by the ATCC number ATCC 69790. As used herein, "ATCC" refers to the American Type Culture Collection international depository located at 10801 University Boulevard, Manassas, Va., 20110–2209, U.S.A. The "ATCC No." is the accession number to cultures on deposit with the ATCC.

DETAILED DESCRIPTION OF THE INVENTION

The present invention describes the bioconversion of a fermentable carbon source for the production of 1,3-propanediol from a single microorganism harboring a dehydratase enzyme. The method incorporates a microorganism containing a dehydratase enzyme which is contacted with a fermentable carbon substrate and 1,3-propanediol is isolated from the growth media. The single organism may be a wild-type organism or may be a genetically altered organism harboring a gene encoding a dehydratase enzyme. The invention further provides new monomers and polymers derived from the biosourced 1,3-propanediol.

Applicants have solved the stated problem and the present invention provides for bioconverting a fermentable carbon source directly to 1,3-propanediol using a single organism. Glucose is used as a model substrate and the bioconversion is applicable to any existing microorganism. Microorganisms harboring the gene for a dehydratase are able to convert glucose and other sugars through the glycerol degradation pathway to 1,3-propanediol with good yields and selectivities. Furthermore, the present invention may be generally applied to include any carbon substrate that is readily converted to glycerol, dihydroxyacetone, or $C_3$ compounds at the oxidation state of glycerol (e.g., glycerol 3-phosphate) or dihydroxyacetone (e.g., dihydroxyacetone phosphate or glyceraldehyde 3-phosphate).

Biologically produced 1,3-propanediol represents a new feedstock for useful polymers, such as 1,3-propanediol polyol and polypropylene terephthalate. Polypropylene terephthalate has not previously been produced from a biosourced monomer. As such, it is a new composition of matter, comprising terephthalate derived from petrochemical sources and 1,3-propane-diol derived from biosourced carbon substrates other than glycerol and dihydroxyacetone. This new polymer may be distinguished from polymer derived from all petrochemical carbon on the basis of dual carbon-isotopic fingerprinting. Additionally, the specific source of biosourced carbon (e.g. glucose vs. glycerol) can be determined by dual carbon-isotopic fingerprinting.

This method usefully distinguishes chemically-identical materials, and apportions carbon in the copolymer by source (and possibly year) of growth of the biospheric (plant) component. The isotopes, $^{14}C$ and $^{13}C$, bring complementary information to this problem. The radiocarbon dating isotope ($^{14}C$), with its nuclear half life of 5730 years, clearly allows one to apportion specimen carbon between fossil ("dead") and biospheric ("alive") feedstocks [Currie, L. A. "Source Apportionment of Atmospheric Particles," *Characterization of Environmental Particles*, J. Buffle and H. P. van Leeuwen, Eds., 1 of Vol. I of the IUPAC Environmental Analytical Chemistry Series (Lewis Publishers, Inc) (1992) 3–74]. The basic assumption in radiocarbon dating is that the constancy of $^{14}C$ concentration in the atmosphere leads to the constancy of $^{14}C$ in living organisms. When dealing with an isolated sample, the age of a sample can be deduced approximately by the relationship $$t=(-5730/0.693)\ln(A/A_O) \qquad \text{(Equation 5)}$$

where t=age, 5730 years is the half-life of radiocarbon, and A and $A_O$ are the specific $^{14}C$ activity of the sample and of the modern standard, respectively [Hsieh, Y., *Soil Sci. Soc. Am J.*, 56, 460, (1992)]. However, because of atmospheric nuclear testing since 1950 and the burning of fossil fuel since 1850, $^{14}C$ has acquired a second, geochemical time characteristic. Its concentration in atmospheric $CO_2$—and hence in the living biosphere—approximately doubled at the peak of nuclear testing, in the mid-1960s. It has since been gradually returning to the steady-state cosmogenic (atmospheric) baseline isotope rate ($^{14}C/^{12}C$) of ca. $1.2\times10^{-12}$, with an approximate relaxation "half-life" of 7–10 years. (This latter half-life must not be taken literally; rather, one must use the detailed atmospheric nuclear input/decay function to trace the variation of atmospheric and biospheric $^{14}C$ since the onset of the nuclear age.) It is this latter biospheric $^{14}C$ time characteristic that holds out the promise of annual dating of recent biospheric carbon. $^{14}C$ can be measured by accelerator mass spectrometry (AMS), with results given in units of "fraction of modern carbon" ($f_M$). $f_M$ is defined by National Institute of Standards and Technology (NIST) Standard Reference Materials (SRMs) 4990B and 4990C, known as oxalic acids standards HOxI and HOxII, respectively. The fundamental definition relates to 0.95 times the $^{14}C/^{12}C$ isotope ratio HOxI (referenced to AD 1950). This is roughly equivalent to decay-corrected pre-Industrial Revolution wood. For the current living biosphere (plant material), $f_M \approx 1.1$.

The stable carbon isotope ratio ($^{13}C/^{12}C$) provides a complementary route to source discrimination and apportionment. The $^{13}C/^{12}C$ ratio in a given biosourced material is a consequence of the $^{13}C/^{12}C$ ratio in atmospheric carbon dioxide at the time the carbon dioxide is fixed and also reflects the precise metabolic pathway. Regional variations also occur. Petroleum, $C_3$ plants (the broadleaf), $C_4$ plants (the grasses), and marine carbonates all show significant differences in $^{13}C/^{12}C$ and the corresponding $\delta^{13}C$ values. Furthermore, lipid matter of $C_3$ and $C_4$ plants analyze differently than materials derived from the carbohydrate components of the same plants as a consequence of the metabolic pathway. Within the precision of measurement, $^{13}C$ shows large variations due to isotopic fractionation effects, the most significant of which for the instant invention is the photosynthetic mechanism. The major cause of differences in the carbon isotope ratio in plants is closely associated with differences in the pathway of photosynthetic carbon metabolism in the plants, particularly the reaction occurring during the primary carboxylation, i.e., the initial fixation of atmospheric $CO_2$. Two large classes of vegetation are those that incorporate the "$C_3$" (or Calvin-Benson) photosynthetic cycle and those that incorporate the "$C_4$" (or Hatch-Slack) photosynthetic cycle. $C_3$ plants, such as hardwoods and conifers, are dominant in the temperate climate zones. In $C_3$ plants, the primary $CO_2$ fixation or carboxylation reaction involves the enzyme ribulose-1,5-diphosphate carboxylase and the first stable product is a 3-carbon compound. $C_4$ plants, on the other hand, include such plants as tropical grasses, corn and sugar cane. In $C_4$ plants, an additional carboxylation reaction involving another enzyme, phosphoenol-pyruvate carboxylase, is the primary carboxylation reaction. The first stable carbon compound is a 4-carbon acid which is subsequently decarboxylated. The $CO_2$ thus released is refixed by the $C_3$ cycle.

Both $C_4$ and $C_3$ plants exhibit a range of $^{13}C/^{12}C$ isotopic ratios, but typical values are ca. −10 to −14 per mil ($C_4$) and −21 to −26 per mil ($C_3$) [Weber et al., *J. Agric. Food Chem.*, 45, 2942 (1997)]. Coal and petroleum fall generally in this latter range. The $^{13}C$ measurement scale was originally defined by a zero set by pee dee belemnite (PDB) limestone, where values are given in parts per thousand deviations from this material. The "$\delta^{13}C$" values are in parts per thousand (per mil), abbreviated ‰, and are calculated as follows (Equation 6):

$$\delta^{13}C \equiv \frac{(^{13}C/^{12}C)_{sample} - (^{13}C/^{12}C)_{standard}}{(^{13}C/^{12}C)_{standard}} \times 100\% \quad \text{(Equation 6)}$$

Since the PDB reference material (RM) has been exhausted, a series of alternative RMs have been developed in cooperation with the IAEA, USGS, NIST, and other selected international isotope laboratories. Notations for the per mil deviations from PDB is $\delta^{13}C$. Measurements are made on $CO_2$ by high precision stable ratio mass spectrometry (IRMS) on molecular ions of masses 44, 45 and 46.

Biosourced 1,3-propanediol and the resulting polyol and polypropylene terephthalate polymer may be completely distinguished from their petrochemical derived counterparts on the basis of $^{14}C$ (fm) and dual carbon-isotopic fingerprinting, indicating new compositions of matter.

1,3-Propanediol and polymers derived therefrom have utility in the production of polyester fibers and the manufacture of polyurethanes. The new monomer and polymer compositions provided by the instant invention additionally may be distinguished on the basis of dual carbon-isotopic fingerprinting from those materials derived solely from petrochemical sources. The ability to distinguish these products is beneficial in tracking these materials in commerce. For example, polymers comprising both "new" and "old" carbon isotope profiles may be distinguished from polymers made only of "old" materials. Hence, the instant materials may be followed in commerce on the basis of their unique profile and for the purposes of defining competition, and for determining shelf life.

The following terms and definitions may be used for interpretation of the claims and specification.

The abbreviation "AMS" refers to accelerator mass spectrometry.

The abbreviation "IRMS" refers to measurements of $CO_2$ by high precision stable isotope ratio mass spectrometry.

The terms "genetically altered" or "genetically altered microorganism" refer to any microorganism, suitable for use in the present invention, which has undergone an alteration of the native genetic machinery of the microorganism. Microorganisms may be genetically altered by undergoing transformation by vectors comprising heterologous nucleic acid fragments, mutagenesis with mutagenizing agents (e.g., UV light, ethanesulfonic acid) or any other method whereby stable alterations of the cell genome occur.

The term "construct" refers to a plasmid, virus, autonomously replicating sequence, genome integrating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "transformation" or "transfection" refers to the acquisition of new genes in a cell after the incorporation of nucleic acid. The acquired genes may be integrated into chromosomal DNA or introduced as extrachromosomal replicating sequences. The term "transformant" refers to the product of a transformation.

The term "expression" refers to the transcription and translation to gene product from a gene coding for the sequence of the gene product.

The term "plasmid" or "vector" or "cosmid" as used herein refers to an extra chromosomal element often carrying genes which are not part of the central metabolism of the cell, and usually in the form of circular double-stranded DNA molecules.

The term "dehydratase enzyme" will refer to any enzyme that is capable of isomerizing or converting a glycerol molecule to the product 3-hydroxypropional. For the purposes of the present invention the dehydratase enzymes include a glycerol dehydratase and a diol dehydratase having preferred substrates of glycerol and 1,2-propanediol, respectively.

The term "carbon substrate" or "carbon source" means any carbon source capable of being metabolized by a microorganism wherein the substrate contains at least one carbon atom, provided that the carbon substrate is other than glycerol or dihydroxyacetone.

The term "biosourced" means a material derived from a biological process as opposed to a synthetic, chemical process. "Biosourced" 1,3-propanediol is derived from a fermentation process from a fermentable carbon source. "Biosourced" polymer or polypropylene terephthalate refers to polymer comprised in whole or in part from biosourced monomer.

The term "polymeric unit" "or repeating unit" means any molecule or combination of molecules that form a polymeric repeating unit. For example, the polymer polypropylene terephthalate is comprised of a repeating unit consisting of 1,3-propanediol and terephthalic acid as shown by formula I:

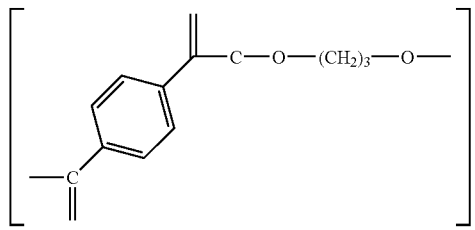

Similarly, the polyol derived from 1,3-propanediol, would have a repeating unit of only 1,3-propanediol.

The term "copolymer" refers to products made by combining repeating units of two or more polymers.

The term "fraction of modern ($f_M$)" is defined by National Institute of Standards and Technology (NIST) Standard Reference Materials (SRMs) 4990B and 4990C, known as oxalic acids standards HOxI and HOxII, respectively. The fundamental definition is 0.95 times the $^{14}C/^{12}C$ isotope ratio HOxI, corrected fro radioactive decay since AD 1950 and adjusted to a $\delta^{13}C(PDB)$ reference value of 19.00 permil. This is roughly equivalent to decay-corrected pre-Industrial Revolution wood.

The term "biogeochemical constraints" refers to the minimum and maximum values for $^{13}C$ and $f_M$ $^{14}C$ likely to occur in nature. These values are derived from statistical reasoning (taking into account factors that bear on measurement errors, population variations, and effects of long term meterological trends) as consistent with scientific reasoning based on the pertinent literature of biology, physics, geology, and chemistry. Specifically, the $f_M$ $^{14}C$ bounds are derived from the observed decay of the nuclear testing pulse in the atmosphere (and biosphere) and from setting the year of growth window to "1990 to present". Thus, the range from the $f_M$ $^{14}C$ bounds for bio-sourced 1,3-propanediol are 1.04 to 1.18; and the range for the $f_M$ $^{14}C$ bounds for bio-sourced polypropylene terephthalate are 0.28 to 0.32. The $^{13}C$ bounds additionally take into account a review of the stable isotope literature, particularly Fritz and Fontes, Ch. 9, P. Fritz and J. Ch. Fontes, eds., Handbook of Environmental Isotope Geochemistry, Elseview, Amsterdam, 1980, vol. 1, chapter 9. Thus, the range for the $\delta^{13}C$ for for bio-sourced 1,3-propanediol are −10.9 to −15.4; and the range for $\delta^{13}C$ bounds for bio-sourced are polypropylene terephthalate.

Construction of Recombinant Organisms:

Recombinant organisms containing the necessary genes that will encode the enzymatic pathway for the conversion of a carbon substrate to 1,3-propanediol may be constructed using techniques well known in the art. In the present invention genes encoding dehydratase enzyme were isolated from a native host such as Klebsiella and used to transform the E. coli host strains DH5α, ECL707 and AA200.

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer directed amplification methods such as polymerase chain reaction (U.S. Pat. No. 4,683,202) to obtain amounts of DNA suitable for transformation using appropriate vectors.

Alternatively, cosmid libraries may be created where large segments of genomic DNA (35–45 kb) may be packaged into vectors and used to transform appropriate hosts. Cosmid vectors are unique in being able to accommodate large quantities of DNA. Generally cosmid vectors have at least one copy of the cos DNA sequence which is needed for packaging and subsequent circularization of the foreign DNA. In addition to the cos sequence these vectors will also contain an origin of replication such as ColE1 and drug resistance markers such as a gene resistant to ampicillin or neomycin. Methods of using cosmid vectors for the transformation of suitable bacterial hosts are well described in Sambrook, J. et al., Molecular Cloning: A Laboratory Manual, Second Edition (1989) Cold Spring Harbor Laboratory Press, herein incorporated by reference.

Typically to clone cosmids, foreign DNA is isolated and ligated, using the appropriate restriction endonucleases, adjacent to the cos region of the cosmid vector. Cosmid vectors containing the linearized foreign DNA is then reacted with a DNA packaging vehicle such as bacteriophage λ. During the packaging process the cos sites are cleaved and the foreign DNA is packaged into the head portion of the bacterial viral particle. These particles are then used to transfect suitable host cells such as E. coli. Once injected into the cell, the foreign DNA circularizes under the influence of the cos sticky ends. In this manner large segments of foreign DNA can be introduced and expressed in recombinant host cells.

Cosmid vectors and cosmid transformation methods were used within the context of the present invention to clone large segments of genomic DNA from bacterial genera known to possess genes capable of processing glycerol to 1,3-propanediol. Specifically, genomic DNA from K. pneumoniae was isolated by methods well known in the art and digested with the restriction enzyme Sau3A for insertion into a cosmid vector Supercos 1™ and packaged using GigapackII packaging extracts. Following construction of the vector E. coli XL1-Blue MR cells were transformed with the cosmid DNA. Transformants were screened for the ability to convert glycerol to 1,3-propanediol by growing the cells in the presence of glycerol and analyzing the media for 1,3-propanediol formation.

Two of the 1,3-propanediol positive transformants were analyzed and the cosmids were named pKP1 and pKP2. DNA sequencing revealed extensive homology to the glycerol dehydratase gene from C. freundii, demonstrating that these transformants contained DNA encoding the glycerol dehydratase gene. Other 1,3-propanediol positive transformants were analyzed and the cosmids were named pKP4 and pKP5. DNA sequencing revealed that these cosmids carried DNA encoding a diol dehydratase gene.

Although the instant invention utilizes the isolated genes from within a *Klebsiella* cosmid, alternate sources of dehydratase genes include, but are not limited to, *Citrobacter*, *Clostridia*, and *Salmonella*.

Other genes that will positively affect the production of 1,3-propanediol may be expressed in suitable hosts. For example it may be highly desirable to over-express certain enzymes in the glycerol degradation pathway and/or other pathways at levels far higher than currently found in wild-type cells. This may be accomplished by the selective cloning of the genes encoding those enzymes into multicopy plasmids or placing those genes under a strong inducible or constitutive promoter. Methods for over-expressing desired proteins are common and well known in the art of molecular biology and examples may be found in Sambrook, supra. Furthermore, specific deletion of certain genes by methods known to those skilled in the art will positively affect the production of 1,3-propanediol. Examples of such methods can be found in *Methods in Enzymology*, Volume 217, R. Wu editor, Academic Press:San Diego 1993.

Mutations and transformations in the 1,3-propanediol production pathway:

Representative enzyme pathway. The production of 1,3-propanediol from glucose can be accomplished by the following series of steps. This series is representative of a number of pathways known to those skilled in the art. Glucose is converted in a series of steps by enzymes of the glycolytic pathway to dihydroxyacetone phosphate (DHAP) and 3-phosphoglyceraldehyde (3-PG). Glycerol is then formed by either hydrolysis of DHAP to dihydroxyacetone (DHA) followed by reduction, or reduction of DHAP to glycerol 3-phosphate (G3P) followed by hydrolysis. The hydrolysis step can be catalyzed by any number of cellular phosphatases which are known to be non-specific with respect to their substrates or the activity can be introduced into the host by recombination. The reduction step can be catalyzed by a $NAD^+$ (or $NADP^+$) linked host enzyme or the activity can be introduced into the host by recombination. It is notable that the dha regulon contains a glycerol dehydrogenase (E.C. 1.1.1.6) which catalyzes the reversible reaction of Equation 3.

Glycerol→3-HP+$H_2O$ (Equation 1)

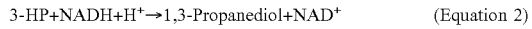

3-HP+NADH+$H^+$→1,3-Propanediol+$NAD^+$ (Equation 2)

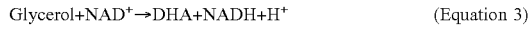

Glycerol+$NAD^+$→DHA+NADH+$H^+$ (Equation 3)

Glycerol is converted to 1,3-propanediol via the intermediate 3-hydroxypropionaldehye (3-HP) as has been described in detail above. The intermediate 3-HP is produced from glycerol, Equation 1, by a dehydratase enzyme which can be encoded by the host or can introduced into the host by recombination. This dehydratase can be glycerol dehydratase (E.C. 4.2.1.30), diol dehydratase (E.C. 4.2.1.28) or any other enzyme able to catalyze this transformation. Glycerol dehydratase, but not diol dehydratase, is encoded by the dha regulon. 1,3-Propanediol is produced from 3-HP, Equation 2, by a $NAD^+$- (or $NADP^+$-) linked host enzyme or the activity can introduced into the host by recombination. This final reaction in the production of 1,3-propanediol can be catalyzed by 1,3-propanediol dehydrogenase (E.C. 1.1.1.202) or other alcohol dehydrogenases.

Mutations and transformations that affect carbon channeling. A variety of mutant organisms comprising variations in the 1,3-propanediol production pathway will be useful in the present invention. For example the introduction of a triosephosphate isomerase mutation (tpi-) into the microorganism of the present invention is an example of the use of a mutation to improve the performance by carbon channeling. The mutation can be directed toward a structural gene so as to impair or improve the activity of an enzymatic activity or can be directed toward a regulatory gene so as to modulate the expression level of an enzymatic activity.

Alternatively, transformations and mutations can be combined so as to control particular enzyme activities for the enhancement of 1,3-propanediol production. Thus it is within the scope of the present invention to anticipate modifications of a whole cell catalyst which lead to an increased production of 1,3-propanediol.

Media and Carbon Substrates:

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. Glycerol production from single carbon sources (e.g., methanol, formaldehyde or formate) has been reported in methylotrophic yeasts (K. Yamada et al., *Agric. Biol. Chem.*, 53:541–543, (1989)) and in bacteria (Hunter et.al., *Biochemistry*, 24:4148–4155, (1985)). These organisms can assimilate single carbon compounds, ranging in oxidation state from methane to formate, and produce glycerol. The pathway of carbon assimilation can be through ribulose monophosphate, through serine, or through xylulose-monophosphate (Gottschalk, *Bacterial Metabolism*, Second Edition, Springer-Verlag: New York (1986)). The ribulose monophosphate pathway involves the condensation of formate with ribulose-5-phosphate to form a 6 carbon sugar that becomes fructose and eventually the three carbon product glyceraldehyde-3-phosphate. Likewise, the serine pathway assimilates the one-carbon compound into the glycolytic pathway via methylenetetrahydrofolate.

In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth Cl Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485–489 (1990)). Hence it is contemplated that the source of carbon utilized in the present invention may encompass a wide variety of carbon containing substrates and will only be limited by the choice of organism.

Although it is contemplated that all of the above mentioned carbon substrates and mixtures thereof are suitable in the present invention, preferred carbon substrates are glucose, fructose, sucrose or methanol.

In addition to an appropriate carbon source, fermentation media must contain suitable minerals, salts, cofactors, buffers and other components, known to those skilled in the art, suitable for the growth of the cultures and promotion of the enzymatic pathway necessary for 1,3-propanediol production. Particular attention is given to Co(II) salts and/or vitamin $B_{12}$ or precursors thereof.

Culture Conditions:

Typically cells are grown at 30° C. in appropriate media. Preferred growth media in the present invention are common commercially prepared media such as Luria Bertani (LB) broth, Sabouraud Dextrose (SD) broth or Yeast medium (YM) broth. Other defined or synthetic growth media may also be used and the appropriate medium for growth of the particular microorganism will be known by someone skilled in the art of microbiology or fermentation science. The use of agents known to modulate catabolite repression directly or indirectly, e.g., cyclic adenosine 2':3'-monophosphate, may also be incorporated into the reaction media. Similarly, the use of agents known to modulate enzymatic activities (e.g., methyl viologen) that lead to enhancement of 1,3-propanediol production may be used in conjunction with or as an alternative to genetic manipulations.

Suitable pH ranges for the fermentation are between pH 5.0 to pH 9.0 where pH 6.0 to pH 8.0 is preferred as the initial condition.

Reactions may be performed under aerobic or anaerobic conditions where anaerobic or microaerobic conditions are preferred.

Batch and Continuous Fermentations:

The present process employs a batch method of fermentation. A classical batch fermentation is a closed system where the composition of the media is set at the beginning of the fermentation and not subject to artificial alterations during the fermentation. Thus, at the beginning of the fermentation the media is inoculated with the desired organism or organisms and fermentation is permitted to occur adding nothing to the system. Typically, however, a "batch" fermentation is batch with respect to the addition of carbon source and attempts are often made at controlling factors such as pH and oxygen concentration. In batch systems the metabolite and biomass compositions of the system change constantly up to the time the fermentation is stopped. Within batch cultures cells moderate through a static lag phase to a high growth log phase and finally to a stationary phase where growth rate is diminished or halted. If untreated, cells in the stationary phase will eventually die. Cells in log phase generally are responsible for the bulk of production of end product or intermediate.

A variation on the standard batch system is the Fed-Batch system. Fed-Batch fermentation processes are also suitable in the present invention and comprise a typical batch system with the exception that the substrate is added in increments as the fermentation progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch fermentations are common and well known in the art and examples may be found in Thomas D. Brock in *Biotechnology: A Textbook of Industrial Microbiology*, Second Edition (1989) Sinauer Associates, Inc., Sunderland, Mass., or Deshpande, Mukund V., *Appl. Biochem. Biotechnol.*, 36:227, (1992), herein incorporated by reference.

Although the present invention is performed in batch mode it is contemplated that the method would be adaptable to continuous fermentation methods. Continuous fermentation is an open system where a defined fermentation media is added continuously to a bioreactor and an equal amount of conditioned media is removed simultaneously for processing. Continuous fermentation generally maintains the cultures at a constant high density where cells are primarily in log phase growth.

Continuous fermentation allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the fermentation. Methods of modulating nutrients and growth factors for continuous fermentation processes as well as techniques for maximizing the rate of product formation are well known in the art of industrial microbiology and a variety of methods are detailed by Brock, supra.

It is contemplated that the present invention may be practiced using either batch, fed-batch or continuous processes and that any known mode of fermentation would be suitable. Additionally, it is contemplated that cells may be immobilized on a substrate as whole cell catalysts and subjected to fermentation conditions for 1,3-propanediol production.

Production of 1,3-propanediol from Glycerol 1,3-Propanediol produced from glycerol is analyzed in the instant invention in order to distinguish it from 1,3-propanediol produced from glucose and other feedstocks.

1,3-Propanediol may be generated from glycerol synthetically via a process that involves (i) dehydration of glycerol over a solid catalyst, (ii) hydration of acrolein that is produced in (i), and catalytic hydrogenation of the reaction mixture, containing 3-hydroxypropionaldehyde and hydroxyacetone, of stage (ii) [see U.S. Pat. No. 5,426,249, hereby incorporated by reference.] Similarly, 1,3-propanediol may be produced by from a reaction mixture of glycerol and synthesis gas in a basic organic solvent in the presence of a tungsten and Group VIII metal-containing catalyst composition (see for example U.S. Pat. No. 4,642,394, hereby incorporated by reference).

1,3-Propanediol may also be produced by biological fermentations. For example, Clostridium sp has been used to ferment glycerol to 1,3-propanediol under standard anaerobic conditions (U.S. Pat. No. 5,254,467) and *Citrobacter sp*. Have been used for the same purpose under similar conditions (U.S. Pat. No. 5,164,309).

Identification and Purification of 1,3-propanediol:

Methods for the purification of 1,3-propanediol from fermentation media are known in the art. For example propanediols can be obtained from cell media by subjecting the reaction mixture to extraction with an organic solvent, distillation and column chromatography (U.S. Pat. No. 5,356,812). A particularly good organic solvent for this process is cyclohexane (U.S. Pat. No. 5,008,473).

1,3-Propanediol may be identified directly by submitting the media to high pressure liquid chromatography (HPLC) analysis. Preferred in the present invention is a method where fermentation media is analyzed on an analytical ion exchange column using a mobile phase of 0.01N sulfuric acid in an isocratic fashion.

For industrial applications, purification of 1,3-propanediol from large volumes of fermentor broth requires non-laboratory scale methods. Difficulties to be overcome include removal of cell matter form the broth (clarification), concentration of 1,3-propanediol either by extraction or water removal and separation of residual impurities from the partially purified monomer.

Broth clarification will typically proceed either by filtration, centrifugation or crossflow microfiltration. Suitable filters are manufactured for example by Millipore (Millipore Corporation, 80 Ashby Road, Bedford, Mass.) or Filmtec (Dow Chemical Co.). Centrifugation effectively removes the bulk of the cells, but, depending upon the nature of the broth, does not always achieve complete cell removal. Crossflow microfiltration yields extremely clear filtrate. The concentrate is a slurry rather than a high-solids cake. The skilled person will be able to adapt the clarification method most appropriate for the fermentation apparatus and conditions being employed.

Water reduction of the clarified broth is complicated by the high solubility of 1,3-propanediol in water. Extraction of 1,3-propanediol from the clarified broth may be accomplished by a variety of methods, including evaporation/distillation, membrane technology, extraction by organic solvent and adsorption.

Rotary evaporators may be used to initially reduce water volume in the clarified broth. This method has enjoyed good success in Applicants' hands. Precipitation of extraneous proteins and salts do not appear to affect 1,3-propanediol recovery Membrane technology may be used either separately or in conjunction with evaporation. Suitable membranes will either (i) allow passage of 1,3-propanediol, retaining water and other feed molecules (ii) allow passage of water and other molecules, retaining 1,3-propanediol or (iii) allow passage of water and 1,3-propanediol while retaining other molecules. In the present invention method (iii) is preferred. Particularly useful, are reverse osmosis membranes such as SW-30–2540 (Filmtec, Dow Chemical Co.) and the DL and SH series of reverse osmosis membranes made by Millipore (Millipore Corporation, Bedford, Mass.).

Following evaporation and membrane concentration, partially purified 1,3-propanediol may be extracted into organic solvents. Suitable solvent will include alcohols such as tert-amyl alcohol, cyclopentanol, octanol, propanol, methanol, and ethanol. Non alcohols may also be used such as octanone, cyclohexane and valeraldehyde. Within the context of the present invention, alcohols are preferred and ethanol is most preferred.

Alternatively 1,3-propanediol may be further concentrated by adsorption to various industrial adsorbents. Activated carbon and polycyclodextrin such as those produced by the American Maize Products Company are particularly suitable.

Following either extraction or adsorption, partially purified 1,3-propanediol must be refined. Refining may be accomplished by electrodialysis (particularly useful for desalting) which utilizes a combination of anion and cation exchange membranes or biopolar (anion and cation) membranes (see for example, Grandison, Alistair S., *Sep. Processes Food Biotechnol. Ind.* (1996), 155–177.)

A preferred method of refining in the present invention is distillation. Distillation may be done in batch where the operating pressure is ambient or below, e.g. about 25 in. Hg of vacuum. Monitoring of distillation indicated that materials evaporated in the order of first to last beginning with light organics, water, diols including 1,3-propanediol and finally heavy materials such as glycerol and precipitated solids.

Cells:

Cells suitable in the present invention comprise those that harbor a dehydratase enzyme. Typically the enzyme will be either a glycerol dehydratase or a diol dehydratase having a substrate specificity for either glycerol or 1,2-propanediol, respectively. Dehydratase enzymes are capable of converting glycerol to hydroxypropionaldehyde (3-HPA) which is then converted to 1,3-propanediol. Cells containing this pathway may include mutated or recombinant organisms belonging to the genera *Citrobacter, Enterobacter, Clostridium, Klebsiella, Samonella,* and *Lactobacillus*. Microorganisms known by persons skilled in the art to produce glycerol by fermentation, e.g., *Aspergillus, Saccharomyces, Zygosaccharomyces, Pichia, Kluyveromyces, Candida, Hansenula, Dunaliella, Debaryomyces, Mucor, Torylopsis,* and *Methylobacteria,* may be the hosts for a recombinant dehydratase enzyme. Other cells suitable as hosts in the present invention include *Bacillus, Escherichia, Pseudomonas* and *Streptomyces*. While not wishing to be bound by theory, it is believed that organisms, belonging to the above mentioned groups, exist in nature that are suitable for the present invention.

On the basis of Applicants' experimental work it is contemplated that a wide variety of cells may be used in the present invention. Applicants have demonstrated for example that cells varying widely in genetic and phenotypic composition are able to bioconvert a suitable carbon substrate to 1,3-propanediol. Cells exemplified include: a *K. pneumoniae* mutant strain constitutive for the dha genes, recombinant *E. coli* strains comprising elements of the *Klebsiella* genome containing genes encoding either glycerol or diol dehydratase, and recombinant *E. coli* (tpi$^-$) strains also transfected with elements of the *Klebsiella* genomes and harboring a mutation in the gene encoding the triosephosphate isomerase enzyme.

Although *E. coli* transformants containing the dha regulon from *Klebsiella pneumonia* were able to convert glycerol to 1,3-propanediol even in the presence of glucose or xylose (Tong et al., *Appl. Biochem. Biotech.,* 34:149 (1992)) no 1,3-propanediol was detected by these organisms in the presence of glucose alone. In direct contrast to this disclosure, Applicants have discovered that three strains of *E. coli,* containing either of two independently isolated cosmids comprising the dha regulon from *Klebsiella pneumonia,* produced 1,3-propanediol from a feed of glucose with no exogenously added glycerol present. *E. coli* strain ECL707, containing cosmid vectors pKP-1 or pKP-2 comprising the *K. pneumoniae* dha regulon, showed detectable though modest production of 1,3-propanediol from glucose in the absence of exogenously added glycerol. Recombinant *E. coli* strains constructed from an alternate host organism, DH5α, also containing cosmid vectors pKP-1 or pKP-2, were found to be more effective than the ECL707 recombinants in producing 1,3-propanediol from glucose under the appropriate conditions. Most effective in producing 1,3-propanediol from glucose were the recombinant *E. coli* strains AA200 containing cosmid vectors pKP-1 or pKP-2. *E. coli* strain AA200 contains a defective triosephosphate isomerase enzyme (tpi$^-$).

A strain of AA200-pKP1, selected for further study from a pool of independent isolates from the transformation reaction, converted glucose to 1,3-propanediol in a two stage reaction. In the first stage, the strain AA200-pKP1–5 was grown to high cell density in the absence of glucose and glycerol. In the second stage, the grown cells, suspended in a medium containing glucose but no glycerol, converted glucose to 1,3-propanediol with high conversion and selectivity. Although differing immunochemically, chromatographically, and genetically, the coenzyme $B_{12}$-dependent enzymes glycerol dehydratase (E.C. 4.2.1.30) and diol dehydratase (E.C. 4.2.1.28) catalyze the conversion of glycerol to 3-hydroxypropionaldehyde. Glycerol dehydratase, but not diol dehydratase, is encompassed by the dha regulon. *K. pneumoniae* ATCC 8724, containing a diol dehydratase but not a glycerol dehydratase converts glycerol to 1,3-propanediol (Forage et al., *J. Bacteriol.*, 149:413, (1982)). Recombinant *E. coli* strains ECL707 and AA200, containing cosmid vector pKP4 encoding genes for a diol dehydratase, converted glucose to 1,3-propanediol.

*K. pneumoniae* ECL2106, prepared by mutagenesis from a naturally occurring strain (Ruch et al., *J. Bacteriol.* 124: 348 (1975)), exhibits constitutive expression of the dha regulon (Ruch et al., supra; Johnson et al., *J. Bacteriol.* 164:479 (1985)). A strain derived from *K. pneumoniae* ATCC 25955, displaying the same phenotype, has been similarly prepared (Forage et al., *J. Bacteriol.* 149:413 (1982)). Expression of the *Klebsiella* dha structural genes is, in part, controlled by a repressor (product of dha R) (Sprenger et al., *J. Gen Microbiol.* 135:1255 (1989)). Applicants have shown that ECL2106, which is constitutive for the dha structural genes, produced 1,3-propanediol from a feed of glucose in the absence of exogenously added glycerol, Example 5. This is in contrast to wild type *K. pneumoniae* ATCC 25955 which did not produce detectable levels of 1,3-propanediol under the same conditions, Example 5.

The expression of the dha structural genes in ECL2106 is further controlled by catabolite expression (Sprenger et al., *J. Gen Microbiol.* 135:1255 (1989)). Elimination of catabolite repression can be achieved by placing the necessary structural genes under the control of alternate promoters as has been demonstrated for 1,3-propanediol oxidoreductase (dhaT) from *C. freundii* and diol dehydratase from *K. oxytoca* ATCC 8724 (Daniel et al., *J. Bacteriol.* 177:2151 (1995) and Tobimatsu et al., *J. Biol. Chem.* 270:7142 (1995)). By eliminating catabolite repression from ECL2106 in this manner, an improvement in the production of 1,3-propanediol from glucose in the absence of an exogenous source of glycerol is achieved. An even further improvement is obtained by appropriate carbon channeling as is described, by example, with the tpi⁻ mutation.

As the dha regulons of *Citrobacter* and *Klebsiella* sp. are strikingly similar, one of skill in the art will appreciate that teachings that involve the production of 1,3-propanediol from glucose in the absence of an exogenous source of glycerol for *Klebsiella* sp. applies to *Citrobacter* sp. as well. Furthermore, as the metabolism of glycerol by *C. butyricum* is comparable to that of *K. pneumoniae* (Zeng et al., *Biotechnol. and Bioeng.* 44:902 (1994)), teachings will extend to *Clostridia* sp. as well.

Sample Preparation Prior to Isotopic Analysis and Isotopic Measurements

Samples subjected to analysis by $^{13}C$ and $^{14}C$ dual isotopic characterization first underwent quantitative combustion of carbon to carbon dioxide. Analysis was accomplished by one of 2 methods, "closed tube" or via commercial "CHN" analyzer. The closed type method involved heating the sample in the presence of CuO, as an oxygen source in a closed tube. The commercial analyzer used molecular oxygen as a oxygen source. Evolving $CO_2$ was purified and submitted for analysis accelerator mass spectrometry (AMS) and isotope ratio mass spectrometry (IRMS).

$^{14}C$ was determined by AMS, using "conventional" graphite targets prepared from the purified $CO_2$. Oxalic acid isotope standards were used for standardization. $^{13}C$ was determined on a split of the purified $CO_2$ samples using an "Optima" isotope ratio mass spectrometer, and the "Craig" algorithm (Allison et al., *Proceedings of a Consultants' Meeting on Reference and intercomparison materials for stable isotopes of light elements* (1993), pp 155–162) operating on the mass 44, 45 and 46 currents. The index used for $^{13}C$ was $\delta^{13}C=[(^{13}C/^{12}C)_{sample}-(^{13}C/^{12}C)_{standard}/(^{13}C/^{12}C)_{standard} \times 1000‰$ [Weber et al., *J. Agric. Food Chem.* 45, 2942, (1997)]. The index used for $^{14}C$ was fraction of modern $(f_M)^{14}C$.

Based on this analysis 1,3-propanediol derived from glucose was found to have a $\delta^{13}C$ of about −13.84‰ to about −13.92‰, and a $f_M$ $^{14}C$ of about 1.11 to about 1.124. 1,3-Propanediol derived from glycerol was found to have a $\delta^{13}C$ of about −22.41‰ to about −22.60‰, and a $f_M$ $^{14}C$ of about 0.85 to about 0.89. In contrast 1,3-propanediol derived from petrochemical sources (acrolein) was found to have a $\delta^{13}C$ of about −17.95‰ to about −18.33‰, and a $f_M$ $^{14}C$ of about −0.004 to about 0.007. Polypropylene terephthalate derived from glucose was found to have a $\delta^{13}C$ of about −24.74‰ to about −24.88‰, and a $f_M$ $^{14}C$ of about 0.299 to about 0.309.

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

EXAMPLES

GENERAL METHODS

Procedures for phosphorylations, ligations and transformations are well known in the art. Techniques suitable for use in the following examples may be found in Sambrook, J. et al., *Molecular Cloning: A Laboratory Manual,* Second Edition, Cold Spring Harbor Laboratory Press (1989).

Materials and methods suitable for the maintenance and growth of bacterial cultures are well known in the art. Techniques suitable for use in the following examples may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994) or Thomas D. Brock in *Biotechnology: A Textbook of Industrial Microbiology,* Second Edition (1989) Sinauer Associates, Inc., Sunderland, Mass. All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Glycerol used in the production of 1,3-propanediol was obtained from J. T. Baker Glycerin USP grade, Lot J25608 and G19657.

NBS19 was used as the standard for $^{13}C$ (see Allison et al., *Proceedings of a Consultants' Meeting on Reference and intercomparison materials for stable isotopes of light elements* (1993), pp 155–162).

NIST SRMs 4990B (HOxI) and 4990C (HOxII) were used as standards for $^{14}C$.

The meaning of abbreviations is as follows: "h" means hour(s), "min" means minute(s), "sec" means second(s), "d" means day(s), "mL" means milliliters, "L" means liters, 50amp is 50 μg/mL ampicillin, and LB-50amp is Luria-Bertani broth containing 50 μg/mL ampicillin.

Within the tables the following abbreviations are used. "Con." is conversion, "Sel." is selectivity based on carbon, and "nd" is not detected.

Enzyme Assays:

Glycerol dehydratase activity in cell free extracts was determined using 1,2-propanediol as substrate. The assay, based on the reaction of aldehydes with methylbenzo-2-thiazolone hydrazone, has been described (Forage and Foster, *Biochim. Biophys. Acta*, 569:249 (1979)). The activity of 1,3-propanediol oxidoreductase, sometimes referred to as 1,3-propanediol dehydrogenase, was determined in solution or in slab gels using 1,3-propanediol and $NAD^+$ as substrates as has also been described. Johnson and Lin, *J. Bacteriol.*, 169:2050 (1987).

Isolation and Identification 1,3-Propanediol:

The conversion of glycerol to 1,3-propanediol was monitored by HPLC. Analyses were performed using standard techniques and materials available to one of skill in the art of chromatography. One suitable method utilized a Waters Maxima 820 HPLC system using UV (210 nm) and RI detection. Samples were injected onto a Shodex SH-1011 column (8 mm×300 mm, purchased from Waters, Milford, Mass.) equipped with a Shodex SH-1011P precolumn (6 mm×50 mm), temperature controlled at 50° C., using 0.01 N $H_2SO_4$ as mobile phase at a flow rate of 0.5 mL/min. When quantitative analysis was desired, samples were prepared with a known amount of trimethylacetic acid as external standard. Typically, the retention times of glycerol (RI detection), 1,3-propanediol (RI detection), and trimethylacetic acid (UV and RI detection) were 20.67 min, 26.08 min, and 35.03 min, respectively.

Production of 1,3-propanediol was confirmed by GC/MS. Analyses were performed using standard techniques and materials available to one of skill in the art of GC/MS. One suitable method utilized a Hewlett Packard 5890 Series II gas chromatograph coupled to a Hewlett Packard 5971 Series mass selective detector (EI) and a HP-INNOWax column (30 m length, 0.25 mm i.d., 0.25 micron film thickness). The retention time and mass spectrum of 1,3-propanediol generated from glycerol were compared to that of authentic 1,3-propanediol (m/e: 57, 58).

Construction of *K. pneumoniae* Cosmid Libraries:

*K. pneumoniae* (ATCC 25955) was grown in 100 ml LB medium for 8 h at 37° C. with aeration. Bacteria (25 mL per tube) were centrifuged at 3,000 rpm for 15 min in a DuPont Sorvall GLC 2.B centrifuge at room temperature. The bacteria were pelleted and supernatant was decanted. The bacterial cell pellet was frozen at −20° C. The chromosomal DNA was isolated as outlined below with special care taken to avoid shearing of DNA (i.e., vortexing was avoided). One tube of bacteria was resuspended in 2.5 mL of 50 mM Tris-10 mM EDTA and 500 μL of lysozyme (1 mg/mL) was added. The pellet was gently resuspended and the suspension was incubated at 37° C. for 15 min. Sodium dodecyl sulfate was added to bring the final concentration to 0.5%. This resulted in the solution becoming clear. Proteinase K (50 μg/mL) was added and the suspension was incubated at 55° C. for 2 h. The tube was removed and transferred to an ice bath and sodium chloride was added to yield a 0.4 M final concentration. Two volumes of ethanol were added to the liquid. A glass tube was inserted to the interface and the DNA was gently spooled. DNA was dipped into a tube containing 70% ethanol. After drying in vacuo, the DNA was resuspended in 500 μL of water and the concentration of DNA was determined spectrophoto-metrically. A diluted aliquot of DNA was run on a 0.5% agarose gel to determine the intact nature of DNA.

The chromosomal DNA was partially digested with Sau3A as outlined by Sambrook et al., supra. DNA (2 μg) was digested with 2 units of Sau3A (Promega, Madison, Wis.) at room temperature in 200 μL of total volume. At 0, 5, 10 and 20 min, samples (50 μL) were removed and transferred to tubes containing 5 umol of EDTA. These tubes were incubated at 70° C. for 10 min. An aliquot (2 μL) was withdrawn and analyzed on a 0.5% agarose gel electrophoresis to determine the level of digestion and the rest of the sample (48 μL) was stored at −20° C. The gel was stained with ethidium bromide and visualized under UV to determine the partial digestion of the chromosomal DNA. A decrease in the size of the chromosomal DNA with increase in time was observed showing that the decrease in the size of the chromosomal DNA is due to the action of Sau3A. DNA was extracted from rest of the sample by standard protocol methods (Sambrook et al., supra).

A cosmid library of partially digested DNA from *K. pneumoniae* was prepared using Supercos cosmid vector kit and GigapackII packaging extracts using reagents purchased from Stratagene (La Jolla, Calif.). The instructions provided by the manufacturer were followed. The packaged *K. pneumoniae* contained $4 \times 10^4$ to $1.0 \times 10^5$ phage titer as determined by transfecting *E. coli* XL1-Blue MR.

Cosmid DNA was isolated from 6 of the *E. coli* transformants and found to contain large insert of DNA (25 to 30 kb).

Example 1

Cloning and transformation of *E. coli* host cells with cosmid DNA for the expression of 1,3-propanediol Media Synthetic S12 medium was used in the screening of bacterial transformants for the ability to make 1,3-propanediol. S12 medium contains: 10 mM ammonium sulfate, 50 mM potassium phosphate buffer, pH 7.0, 2 mM $MgCl_2$, 0.7 mM $CaCl_2$, 50 μM $MnCl_2$, 1 μM $FeCl_3$, 1 μM ZnCl, 1.7 μM $CuSO_4$, 2.5 μM $CoCl_2$, 2.4 μM $Na_2MoO_4$, and 2 μM thiamine hydrochloride.

Medium A used for growth and fermentation consisted of: 10 mM ammonium sulfate; 50 mM MOPS/KOH buffer, pH 7.5; 5 mM potassium phosphate buffer, pH 7.5; 2 mM $MgCl_2$; 0.7 mM $CaCl_2$; 50 μM $MnCl_2$; 1 μM $FeCl_3$; 1 μM ZnCl; 1.72 μM $CuSO_4$; 2.53 μM $CoCl_2$; 2.42 μM $Na_2MoO_4$; 2 μM thiamine hydrochloride; 0.01% yeast extract; 0.01% casamino acids; 0.8 μg/mL vitamin $B_{12}$; and 50amp. Medium A was supplemented with either 0.2% glycerol or 0.2% glycerol plus 0.2% D-glucose as required.

Cells:

Klebsiella pneumoniae ECL2106 (Ruch et al., *J. Bacteriol.*, 124, 348 (1975)), also known in the literature as *K. aerogenes* or *Aerobacter aerogenes*, was obtained from E. C. C. Lin (Harvard Medical School, Cambridge, Mass.) and was maintained as a laboratory culture.

Klebsiella pneumoniae ATCC 25955 was purchased from American Type Culture Collection (Manassas, Va.).

*E. coli* DH5α was purchased from Gibco/BRL and was transformed with the cosmid DNA isolated from *Klebsiella pneumoniae* ATCC 25955 containing a gene coding for either a glycerol or diol dehydratase enzyme. Cosmids containing the glycerol dehydratase were identified as pKP1 and pKP2 and cosmid containing the diol dehydratase enzyme were identified as pKP4. Transformed DH5α cells were identified as DH5α-pKP1, DH5α-pKP2, and DH5α-pKP4.

*E. coli* ECL707 (Sprenger et al., *J. Gen. Microbiol.*, 135, 1255 (1989)) was obtained from E. C. C. Lin (Harvard Medical School, Cambridge, Mass.) and was similarly transformed with cosmid DNA from *Klebsiella pneumoniae*. These transformants were identified as ECL707-pKP1 and ECL707-pKP2, containing the glycerol dehydratase gene and ECL707-pKP4 containing the diol dehydratase gene.

*E. coli* AA200 containing a mutation in the tpi gene (Anderson et al., *J. Gen Microbiol.*, 62, 329 (1970)) was purchased from the *E. coli* Genetic Stock Center, Yale University (New Haven, Conn.) and was transformed with *Klebsiella* cosmid DNA to give the recombinant organisms AA200-pKP 1 and AA200-pKP2, containing the glycerol dehydratase gene, and AA200-pKP4, containing the diol dehydratase gene.

DH5α:

Six transformation plates containing approximately 1,000 colonies of *E. coli* XL1-Blue MR transfected with *K. pneumoniae* DNA were washed with 5 mL LB medium and centrifuged. The bacteria were pelleted and resuspended in 5 mL LB medium+glycerol. An aliquot (50 μL) was inoculated into a 15 mL tube containing S12 synthetic medium with 0.2% glycerol+400 ng per mL of vitamin $B_{12}$+0.001% yeast extract+50amp. The tube was filled with the medium to the top and wrapped with parafilm and incubated at 30° C. A slight turbidity was observed after 48 h. Aliquots, analyzed for product distribution as described above at 78 h and 132 h, were positive for 1,3-propanediol, the later time points containing increased amounts of 1,3-propanediol.

The bacteria, testing positive for 1,3-propanediol production, were serially diluted and plated onto LB-50amp plates in order to isolate single colonies. Forty eight single colonies were isolated and checked again for the production of 1,3-propanediol. Cosmid DNA was isolated from 6 independent clones and transformed into *E. coli* strain DH5α. The transformants were again checked for the production of 1,3-propanediol. Two transformants were characterized further and designated as DH5α-pKP1 and DH5α-pKP2.

A 12.1 kb EcoRI-SalI fragment from pKP1, subcloned into pIBI31 (IBI Biosystem, New Haven, Conn.), was sequenced and termed pHK28–26 (SEQ ID NO:1). Sequencing revealed the loci of the relevant open reading frames of the dha operon encoding glycerol dehydratase and genes necessary for regulation. Referring to SEQ ID NO:1, a fragment of the open reading frame for dhaK encoding dihydroxyacetone kinase is found at bases 1–399; the open reading frame dhaD encoding glycerol dehydrogenase is found at bases 983–2107; the open reading frame dhaR encoding the repressor is found at bases 2209–4134; the open reading frame dhaT encoding 1,3-propanediol oxidoreductase is found at bases 5017–6180; the open reading frame dhaB1 encoding the alpha subunit glycerol dehydratase is found at bases 7044–8711; the open reading frame dhaB2 encoding the beta subunit glycerol dehydratase is found at bases 8724–9308; the open reading frame dhaB3 encoding the gamma subunit glycerol dehydratase is found at bases 9311–9736; and the open reading frame dhaBX, encoding a protein of unknown function is found at bases 9749–11572.

Single colonies of *E. coli* XL1-Blue MR transfected with packaged cosmid DNA from *K. pneumoniae* were inoculated into microtiter wells containing 200 uL of S15 medium (ammonium sulfate, 10 mM; potassium phosphate buffer, pH 7.0, 1 mM; MOPS/KOH buffer, pH 7.0, 50 mM; $MgCl_2$, 2 mM; $CaCl_2$, 0.7 mM; $MnCl_2$, 50 uM; $FeCl_3$, 1 uM; ZnCl, 1 uM; $CuSO_4$, 1.72 uM; $CoCl_2$, 2.53 uM; $Na_2MoO_4$, 2.42 uM; and thiamine hydrochloride, 2 uM)+0.2% glycerol+400 ng/mL of vitamin $B_{12}$+0.001% yeast extract+50 ug/mL ampicillin. In addition to the microtiter wells, a master plate containing LB-50amp was also inoculated. After 96 h, 100 uL was withdrawn and centrifuged in a Rainin microfuge tube containing a 0.2 micron nylon membrane filter. Bacteria were retained and the filtrate was processed for HPLC analysis. Positive clones demonstrating 1,3-propanediol production were identified after screening approximately 240 colonies. Three positive clones were identified, two of which had grown on LB-50amp and one of which had not. A single colony, isolated from one of the two positive clones grown on LB-50amp and verified for the production of 1,3-propanediol, was designated as pKP4. Cosmid DNA was isolated from *E. coli* strains containing pKP4 and *E. coli* strain DH5α was transformed. An independent transformant, designated as DH5α-pKP4, was verified for the production of 1,3-propanediol.

ECL707:

*E. coli* strain ECL707 was transformed with cosmid *K. pneumoniae* DNA corresponding to pKP1, pKP2, pKP4 and the Supercos vector alone and named ECL707-pKP1, ECL707-pKP2, ECL707-pKP4, and ECL707-sc, respectively. ECL707 is defective in glpK, gld, and ptsD which encode the ATP-dependent glycerol kinase, $NAD^+$-linked glycerol dehydrogenase, and enzyme II for dihydroxyacetone of the phosphoenolpyruvate dependent phosphotransferase system, respectively.

Twenty single colonies of each cosmid transformation and five of the Supercos vector alone (negative control) transformation, isolated from LB-50amp plates, were transferred to a master LB-50amp plate. These isolates were also tested for their ability to convert glycerol to 1,3-propanediol in order to determine if they contained dehydratase activity. The transformants were transferred with a sterile toothpick to microtiter plates containing 200 μL of Medium A supplemented with either 0.2% glycerol or 0.2% glycerol plus 0.2% D-glucose. After incubation for 48 hr at 30° C., the contents of the microtiter plate wells were filtered through an 0.45 μ nylon filter and chromatographed by HPLC. The results of these tests are given in Table 1.

TABLE 1

Conversion of glycerol to 1,3-propanediol by transformed ECL707: number of positive isolates/number of isolates tested

| Transformant | Glycerol | Glycerol plus Glucose |
|---|---|---|
| ECL707-pKP1 | 19/20 | 19/20 |
| ECL707-pKP2 | 18/20 | 20/20 |
| ECL707-pKP4 | 0/20 | 20/20 |
| ECL707-sc | 0/5 | 0/5 |

AA200:

*E. coli* strain AA200 was transformed with cosmid *K. pneumoniae* DNA corresponding to pKP1, pKP2, pKP4 and the Supercos vector alone and named AA200-pKP1, AA200-pKP2, AA200-pKP4, and AA200-sc, respectively. Strain AA200 is defective in triosephosphate isomerase, (tpi$^-$).

Twenty single colonies of each cosmid transformation and five of the empty vector transformation were isolated and tested for their ability to convert glycerol to 1,3-propanediol as described for *E. coli* strain ECL707. The results of these tests are given in Table 2.

TABLE 2

Conversion of glycerol to 1,3-propanediol by transformed AA200: Number of positive isolates/number of isolates tested

| Transformant | Glycerol | Glycerol plus Glucose |
|---|---|---|
| AA200-pKP1 | 17/20 | 17/20 |
| AA200-pKP2 | 17/20 | 17/20 |
| AA200-pKP4 | 2/20 | 16/20 |
| AA200-sc | 0/5 | 0/5 |

Example 2

Conversion of D-glucose to 1.3-propanediol by *E. coli* strain AA200, transformed with *Klebsiellia pneumoniae* DNA containing dehydratase activity Glass serum bottles, filled to capacity with media (ca. 14 mL of Medium A as defined in Example 1 supplemented with 10 μg/mL kanamycin and 0.2% D-glucose, plus or minus 0.5–1.0 mM cyclic adenosine 2':3'-monophosphate (cAMP)), were inoculated with selected single colony isolates of *E. coli* strain AA200 containing the *K. pneumoniae* dha regulon cosmids pKP1 or pKP2, the *K. pneumoniae* pdu operon pKP4, or the Supercos vector alone. In order to avoid contact with glycerol, the innoculation was performed from either an agar plate of LB-50amp or from a liquid culture of the same medium. The reactions were incubated for ca. 72 hr at 30° C. while shaking at 250 rpm. Growth was determined by the change in absorbance at 600 nm where the initial $OD_{600}$ was 0.020 AU. The extent of glucose depletion and product distribution were determined by HPLC. Single colony isolates are identified by a numbered suffix "-x", e.g., AA200-pKP1-x. Cumulative results are presented in Table 3 and Table 4.

TABLE 3

Conversion of 0.2% D-glucose to 1,3-propanediol by transformed *E. coli* strain AA200: without cAMP

| Transformant | $OD_{600}$ | [1,3-propane-diol] (mM) | Con. (%) | Sel. (%) |
|---|---|---|---|---|
| AA200-pKP1-3 | 0.056 | 0.05 | 17 | 1 |
| AA200-pKP1-5 | 0.115 | nd | 0 | |
| " | 0.007 | nd | 0 | |
| " | 0.076 | 0.2 | 14 | 5 |
| AA200-pKP1-20 | 0.116 | nd | 27 | 0 |
| " | 0.205 | 0.3 | 17 | 8 |
| AA200-pKP2-10 | 0.098 | 0.2 | 13 | 7 |
| AA200-pKP2-14 | 0.117 | 0.5 | 17 | 14 |
| " | 0.129 | 0.2 | 19 | 5 |
| AA200-pKP2-20 | 0.094 | nd | 11 | 0 |
| AA200-pKP4-4 | 0.198 | 0.1 | 28 | 2 |
| AA200-pKP4-19 | 0.197 | 0.2 | 34 | 3 |
| AA200-pKP4-20 | 0.206 | 0.1 | 38 | 1 |
| AA200-sc-1 | 0.097 | nd | 22 | 0 |
| " | 0.176 | nd | 46 | 0 |

TABLE 4

Conversion of 0.2% D-glucose to 1,3-propanediol by transformed *E. coli* strain AA200: with cAMP

| Transformant | $OD_{600}$ | [1,3-propane-diol] (mM) | % Con. | % Sel. |
|---|---|---|---|---|
| AA200-pKP1-3 | 0.102 | 0.5 | 19 | 12 |
| AA200-pKP1-5 | 0.088 | 1.5 | 21 | 37 |
| " | 0.236 | 1.4 | 24 | 28 |
| " | 0.071 | 0.8 | 15 | 23 |
| AA200-pKP1-20 | 0.153 | nd | 40 | 0 |
| " | 0.185 | 0.9 | 27 | 16 |
| AA200-pKP2-10 | 0.098 | 0.2 | 13 | 7 |
| AA200-pKP2-14 | 0.213 | 2.0 | 26 | 27 |
| " | 0.155 | 0.6 | 25 | 12 |
| AA200-pKP2-20 | 0.198 | 1.2 | 40 | 14 |
| AA200-pKP4-4 | 0.218 | 0.1 | 31 | 2 |
| AA200-pKP4-19 | 0.223 | 0.2 | 37 | 3 |
| AA200-pKP4-20 | 0.221 | 0.2 | 35 | 3 |
| AA200-sc-1 | 0.111 | nd | 23 | 0 |
| " | 0.199 | nd | 49 | 0 |
| " | 0.122 | nd | 25 | 0 |

[a]The identity of 1,3-propanediol was verified by GC/MS as described in the GENERAL METHODS.

Example 3

Conversion of D-glucose to 1,3-propanediol by *E. coli* strain DH5α, transformed with *Klebsiella pneumoniae* DNA containing dehydratase activity

*E. coli* strain DH5α, containing the *K. pneumoniae* dha regulon cosmids pKP1 or pKP2, were tested for their ability to convert D-glucose to 1,3-propanediol as described in Example 2. The results are presented in Table 5.

TABLE 5

Conversion of 0.2% D-glucose to 1,3-propanediol by transformed *E. coli* strain DH5α: plus (+) and minus (−) cAMP

| Transformant | $OD_{600}$ | [1,3-propane-diol] (mM) | % Con. | % Sel. |
|---|---|---|---|---|
| DH5α-pKP1 (−) | 0.630 | 0.5 | 100 | 2 |
| DH5α-pKP1 (+) | 0.774 | 0.6 | 100 | 3 |

TABLE 5-continued

Conversion of 0.2% D-glucose to 1,3-propanediol
by transformed E. coli strain DH5α:
plus (+) and minus (−) cAMP

| Transformant | OD$_{600}$ | [1,3-propane-diol] (mM) | % Con. | % Sel. |
|---|---|---|---|---|
| DH5α-pKP2 (−) | 0.584 | 0.6 | 100 | 3 |
| DH5α-pKP2 (+) | 0.699 | 0.7 | 100 | 3 |

Example 4

Conversion of D-glucose to 1,3-propanediol by *E. coli* strain ECL707, transformed with *Klebsiellia pneumoniae* DNA containing dehydratase activity

*E. coli* strain ECL707, containing the *K. pneumoniae* dha regulon cosmids pKP1 or pKP2, the *K. pneumoniae* pdu operon pKP4, or the Supercos vector alone, were tested for their ability to convert D-glucose to 1,3-propanediol as described in Example 2. In each case, conversion was quantitative. The results are presented in Table 6.

TABLE 6

Conversion of D-glucose to 1,3-propanediol by
transformed E. coli strain ECL707: with and without cAMP

| Transformant | OD$_{600}$ (without cAMP) | [1,3-propane-diol] (mM) (without cAMP) | OD$_{600}$ (with cAMP) | [1,3-propane-diol] (mM) (with cAMP) |
|---|---|---|---|---|
| ECL707-pKP1-1 | 0.607 | 0.1 | 0.475 | 0.1 |
| ECL707-pKP1-3 | 0.619 | 0.1 | 0.422 | 0.1 |
| ECL707-pKP1-7 | 0.582 | 0.2 | 0.522 | 0.2 |
| ECL707-pKP1-10 | 0.593 | 0.1 | 0.408 | 0.1 |
| ECL707-pKP1-18 | 0.584 | 0.1 | 0.433 | 0.1 |
| ECL707-pKP2-4 | 0.588 | 0.1 | 0.408 | 0.1 |
| ECL707-pKP2-5 | 0.630 | 0.1 | 0.516 | 0.2 |
| ECL707-pKP2-8 | 0.542 | 0.1 | 0.486 | 0.1 |
| ECL707-pKP2-15 | 0.589 | 0.1 | 0.485 | 0.1 |
| ECL707-pKP2-19 | 0.577 | 0.1 | 0.504 | 0.1 |
| ECL707-pKP4-8 | 0.499 | nd | 0.361 | <0.1 |
| ECL707-pKP4-9 | 0.544 | nd | 0.354 | nd |
| ECL707-pKP4-10 | 0.515 | nd | 0.265 | <0.1 |
| ECL707-pKP4-14 | 0.512 | nd | 0.318 | <0.1 |
| ECL707-pKP4-17 | 0.545 | nd | 0.388 | <0.1 |
| ECL707-sc-1 | 0.592 | nd | 0.385 | nd |

Example 5

Conversion of D-glucose to 1,3-propanediol under fermentation conditions

*E. coli* strain ECL707, containing the *K. pneumoniae* dha regulon cosmids pKP1 or pKP2, the *K. pneumoniae* pdu operon pKP4, or the Supercos vector alone, is grown in a 5 L Applikon fermenter for the production of 1,3-propanediol from glucose.

The medium used contains 50–100 mM potassium phosphate buffer, pH 7.5, 40 mM $(NH_4)_2SO_4$, 0.1% (w/v) yeast extract, 10 µM $CoCl_2$, 6.5 µM $CuCl_2$, 100 µM $FeCl_3$, 18 µM $FeSO_4$, 5 µM $H_3BO_3$, 50 µM $MnCl_2$, 0.1 µM $Na_2MoO_4$, 25 µM $ZnCl_2$, 0.82 mM $MgSO_4$, 0.9 mM $CaCl_2$, and 10–20 g/L glucose. Additional glucose is fed, with residual glucose maintained in excess. Temperature is controlled at 37° C. and pH controlled at 7.5 with 5N KOH or NaOH. Appropriate antibiotics are included for plasmid maintenance. For anaerobic fermentations, 0.1 vvm nitrogen is sparged through the reactor; when the dO setpoint was 5%, 1 vvm air is sparged through the reactor and the medium is supplemented with vitamin $B_{12}$.

Titers of 1,3-propanediol (g/L) range from 8.1 to 10.9. Yields of 1,3-propandiol (g/g) range from 4% to 17%.

Example 6

Purification of Biosourced 1,3-Propanediol 1,3-Propanediol, produced as recited in Examples 2–5, was purified, by a multistep process including broth clarification, rotary evaporation, anion exchange and multiple distillation of the supernatant.

At the end of the fermentation, the broth was clarified using a combination of centrifugation and membrane filtration for cell separation, followed by ultrafiltration through a 1000 MW membrane. The clarified broth processed in a large rotary evaporator. Approximately 46 pounds of feed material (21,000 grams) were processed to a concentrated syrup. A 60 ml portion of syrup was placed in the still pot of a 1" diameter distillation column. Distillation was conducted at a vacuum of 25 inches of mercury. A reflux ratio of approximately 1 was used throughout the distillation. Several distillate cuts were taken, the central of which received further processing. The material was diluted with an equal volume of water, the material was loaded onto an anion exchange column (mixed bed, 80 grams of NM-60 resin), which had been water-washed. Water was pumped at a rate of 2 ml/min, with fractions being collected every 9 minutes. Odd number fractions were analyzed, and fractions 3 through 9 contained 3G. The fractions containing 3G were collected and subjected to microdistillation to recover several grams of pure 1,3-propanediol monomer (which was polymerized to polypropylene terephthalate according the method described in Example 7.

Example 7

Polymerization of Biosourced 1,3-Propanediol to Polypropylene Terephthalate

Dihydroxypropyl terephthalate, purified according to the method recited in Example 6 was produced from dimethyl terephthalate as a polypropylene terephthalate monomer according to the following process.

Dimethyl terephthalate (150 g) and biosourced 1,3-propanediol are mixed together with titanium isopropoxide (registry number 546–68–9) (0.03 mL) in a 1-liter flask equipped with a stirrer, a thermometer and a 13-inch Vigreaux condenser leading to a distillation head. The mixture is blanketed with nitrogen and heated to react the components and distill off the methanol reaction by-product. After about 5 h, 61 mL of methanol distilled off, close to the stoichiometric quantity expected. This dihydroxy propyl terephthalate is then cast into an aluminum tray and allowed to solidify.

Preparation of dihydroxypropyl terephthalate from terephthalic acid as a polypropylene terephthalate monomer:

A 100-mL round bottom flask equipped with a stir bar, nitrogen source and a distillation head was charged with terephthalic acid (33.2 g) and 1,3-propanediol (30.4 g, Example 2). The reaction was heated with stirring under nitrogen to distill water and 1,3-propanediol from the mixture, until no further distillate appeared in the receiving flask, and the terephthalic acid is in solution. This result typically occurs after 20 to 28 h. The pressure was then reduced in the flask by means of a vacuum pump to distill additional water and 1,3-propanediol as the esterification takes place. The esterification was judged as being complete when the 1,3-propanediol and water cease to distill, typically 2 h at 25 mm Hg pressure. The reaction mixture was clear, indicating that the terephthalic acid had dissolved and esterified. The molten terephthalic acid/1,3-propanediol oligomer was then cast from the flask into an aluminum pan under nitrogen and allowed to solidify.

Polymerization of dihydroxypropyl terephthalate to polypropylene terephthalate:

A 500-mL round bottom reaction flask equipped with a distillation head, mechanical stirrer, nitrogen source, and a vacuum source was charged with 150 g of the dihydroxypropyl terephthalate monomer, prepared as described in either of the two procedures above. The polymerization catalyst, titanium isopropoxide (0.022 mL), was then added to the reaction bath. The flask was immersed in a molten metal bath equilibrated at 255° C. Stirring at 50 rpm commenced as soon as the monomer melted, and the melt was held at 255° C. and 1 atm of pressure for 30 min. The pressure was then reduced to 120 mm Hg pressure for 20 min, then to 20 mm Hg for 10 min, and then to 10 mm Hg for an additional 10 min. Finally, the pressure was reduced to less than 1 mm Hg for the duration of the polymerization, as indicated by a torque rise, which occurred after an additional 1 h, yielding higher molecular weight polypropylene terephthalate.

Example 8

Dual Isotopic Characterization—Distinct Product Characterization

Example 8 demonstrates that biosourced 1,3-propanediol and its polymer derivative may be distinguished from monomer and polymers derived solely from petrochemical sources.

Samples analyzed by $^{13}C$ and $^{14}C$ dual isotopic characterization are listed in Table 7 and included glucose (samples 1, 2), polypropylene terephthalate produced from glucose (samples 3, 4), 1,3-propanediol produced from glucose (sample 5), 1,3-propanediol produced from glycerol (sample 6, see Example 1, Table 1) and 1,3-propanediol produced from petrochemical feedstock (samples 7, 8).

Petrochemical derived 1,3-propanediol was obtained from Degussa Aktiengesellschaft (Frankfurt, Federal Republic of Germany) and prepared obtained by hydration of acrolein to 3-hydroxypropionaldehyde with subsequent catalytic hydrogenation, according to the process described in U.S. Pat. No. 5,364,987, hereby incorporated by reference.

Sample Preparation Prior to Isotopic Analysis (combustion):

The first step comprises quantitative combustion of the sample carbon to carbon dioxide. Two alternate routes were used for this oxidation: (1) use of closed tube (CT) combustion, heating the sample to 900° C. in a quartz tube with CuO as the oxygen source; (2) using a specially adapted commercial "CHN" analyzer for a $CO_2$ trapping system. In the latter case, the oxygen source was molecular (tank) oxygen. Recovery of test materials was evaluated for both systems, based on pure substance stoichiometry. Sample $CO_2$ was purified and sealed in quartz tubes and submitted for isotopic measurement by AMS and IRMS. As these samples were all in the form of $CO_2$, "memory" of the original chemical substances was totally erased. The amounts of material oxidized ranged from ca. 0.6 to 2.0 mg carbon, quantities suitable for high precision measurement.

Isotopic Measurements:

$^{14}C$ was determined by AMS, using "conventional" graphite targets prepared from the $CO_2$. The accelerator employed was the NSF AMS facility, based on 2 MV tandem AMS with monitoring of $C^{3+}$ atomic $^{13}C$ and $^{14}C$ high energy ions. Both HOxI and HoxII standards were used, affording the opportunity to check the precision and bias of the process by monitoring the HOxII/HOxI ratio. Typically for AMS measurements at the mg level, this measured ratio is stable to ca. 1%.

$^{13}C$ was determined on a split of the $CO_2$ samples using an "Optima" isotope ratio mass spectrometer, and the "Craig" algorithm (Allison et al., Proceedings of a Consultants' Meeting on Reference and intercomparison materials for stable isotopes of light elements (1993), pp 155–162) operating on the mass 44, 45 and 46 currents.

$^{13}C/^{12}C$ and $^{14}C$ Isotope Characterization:

Petrochemicals have $\delta^{13}$ values of approximately −27.5‰, while C3 derived sugars have $\delta^{13}$ values of −24‰ and C4 derived sugars have $\delta^{13}$ values of −14‰, using the NBS standard (see Coplen et al., *EOS, Transactions, American Geophysical Union* 77, 27,255, (1996). On this basis, it was anticipated that 1,3-propanediol would have $\delta^{13}$ values similar to the corn starch from which it is derived and $f_M$ values similar to modern carbon. Similarly, the polypropylene terephthalate derived from biosourced 1,3-propanediol will have $\delta^{13}$ values for the glycol component similar to the corn starch while the terephthaloyl component will be similar to petrochemicals.

$^{13}C$ and $^{14}C$ data for dual isotopic characterization experiments of the above mentioned samples are given in Table 7, and shown graphically in FIG. 1. It is clear that complete discrimination has been achieved for all samples, including those that are identical chemically. Isotope differences were so great, compared to the internal reproducibility, that for these particular materials either isotope would have been sufficient to make a differentiation.

$^{14}C$ provides the potential for "absolute" year-of-growth discrimination, as well as biospheric-fossil apportionment of the test materials, using the $^{14}C$ input/decay function discussed previously. $^{13}C$ is interesting especially as an indicator of C3 or C4 plant origin material. For example, Table 7 and FIG. 1 illustrate the following:

What is claimed is:

1. Biosourced 1,3-propanediol produced by a process comprising the steps of:
   (i) contacting a medium containing at least one fermentable carbon substrate with a single microorganism to yield a culture medium, the at least one carbon substrate is glucose, or oligosaccharides and polysaccharides that contain glucose and not glycerol or dihydroxyacetone, and the single microorganism is selected from the group consisting of *Klebsiella, Citrobacter,* and *Escherichia*, transformed with a gene encoding a diol dehydratase enzyme or a glycerol dehydratase enzyme,
   (ii) incubating the culture medium of step (i) under suitable conditions to produce 1,3-propanediol; and
   (iii) recovering biosourced 1,3-propanediol from the culture medium wherein said biosourced 1,3-propanediol has a $\delta^{13}$C of −15.4 greater.

2. Biosourced 1,3-propanediol produced by a process comprising the steps of:
   (i) contacting a culture medium containing glucose with a recombinant *Escherichia coil* transformed with a gene encoding a diol dehydratase enzyme or a glycerol dehydratase enzyme;
   (ii) incubating the culture medium of step (i) under suitable conditions to produce biosourced 1,3-propanediol; and biosourced recovering 1,3-propanediol from the culture medium
   wherein said biosourced 1,3-propanediol has a $\delta^{13}$C of −15.4 or greater.

3. Biosourced 1,3-propanediol produced by the process of claims 1 or 2 having a $\delta^{13}$C of about −13.84 to about −13.92, and a $f_M{}^{14}$C of about 1.111 to about 1.124.

4. A polymer comprising at least two repeating units of biosourced 1,3-propanediol characterized by a $\delta^{13}$C of about −13.84 to about −13.92, and a $f_M{}^{14}$C of about 1.111 to about 1.124.

5. A polymer comprising at least two repeating units of biosourced polypropylene terephthalate, said polypropylene terephthalate having $\delta^{13}$C of about −24.74 to about −24.88, and a $f_M{}^{14}$C of about 0.299 to about 0.309.

6. A co-polymer comprising a blend of two or more polymers, at least one of the polymers comprising biosourced 1,3-propanediol characterized by a $\delta^{13}$C of about −13.84 to about −13.92, and a $f_M{}^{14}$C of about 1.111 to about 1.124.

7. An article of manufacture comprising the polymer or co-polymer of any one of claims 4,5, or 6, said article of manufacture in a form selected from the group consisting of a film, fiber, a particle, a package, and a molded article.

8. An article of manufacture comprising biosourced 1,3-Propanediol produced by the process of claims 1 or 2 said article of manufacture in a form selected from the group consisting of a film, fiber, a particle, a package, and a molded article.

* * * * *